US007043474B2

(12) United States Patent
Mojsilovic et al.

(10) Patent No.: US 7,043,474 B2
(45) Date of Patent: May 9, 2006

(54) SYSTEM AND METHOD FOR MEASURING IMAGE SIMILARITY BASED ON SEMANTIC MEANING

(75) Inventors: Aleksandra Mojsilovic, New York, NY (US); Bernice Rogowitz, Ossining, NY (US); Jose Gomes, Douglaston, NY (US)

(73) Assignee: International Business Machines Corporation, Armonk, NY (US)

( * ) Notice: Subject to any disclaimer, the term of this patent is extended or adjusted under 35 U.S.C. 154(b) by 563 days.

(21) Appl. No.: 10/123,334

(22) Filed: Apr. 15, 2002

(65) Prior Publication Data

US 2003/0195883 A1 Oct. 16, 2003

(51) Int. Cl.
*G06F 17/30* (2006.01)

(52) U.S. Cl. .............................. 707/6; 707/10; 382/173; 382/159

(58) Field of Classification Search ................ 707/3–6, 707/10, 102, 104.1; 709/203, 219; 382/164, 382/171, 173, 175, 180, 159
See application file for complete search history.

(56) References Cited

U.S. PATENT DOCUMENTS

| | | | | |
|---|---|---|---|---|
| 5,899,999 | A * | 5/1999 | De Bonet | 707/104.1 |
| 5,915,250 | A * | 6/1999 | Jain et al. | 707/100 |
| 6,240,423 | B1 * | 5/2001 | Hirata | 707/104.1 |
| 6,484,149 | B1 * | 11/2002 | Jammes et al. | 705/26 |
| 6,721,449 | B1 * | 4/2004 | Krishnamachari | 382/165 |
| 6,804,684 | B1 * | 10/2004 | Stubler et al. | 707/104.1 |
| 2002/0131641 | A1 | 9/2002 | Luo et al. | 382/218 |
| 2003/0053693 | A1 * | 3/2003 | Chatting et al. | 382/181 |
| 2004/0221237 | A1 * | 11/2004 | Foote et al. | 715/700 |
| 2005/0010553 | A1 * | 1/2005 | Liu | 707/1 |

OTHER PUBLICATIONS

Mojsilovic et al., "Capturing Image Semantics With Low-Level Descriptors", Proc. IEEE International Conference on Image Processing, ICIP 2001, Thessaloniki Greece, Oct. 2001.

Chang E Tal., "Semantic Visual Templates: Linking Visual Features to Semantics", Proc. IEEE International Conference of Image Processing, Chicago, Illinois, pp. 531-535, 1995.

Wang et al., "SIMPLIcity: Semantics-Sensitive Integrated Matching for Picture Libraries", IEEE Transaction on Pattern Analysis and Machine Intelligence, vol. 23, No. 9, Sep. 2001.

(Continued)

*Primary Examiner*—Lelsie Wong
(74) *Attorney, Agent, or Firm*—Louis P. Herzberg; Harrington & Smith, LLP

(57) ABSTRACT

A method includes deriving a plurality of semantic categories for representing important semantic cues in images, where each semantic category is modeled through a combination of perceptual features that define the semantics of that category and that discriminate that category from other categories; for each semantic category, forming a set of the perceptual features comprising required features and frequently occurring features; comparing an image to said semantic categories; and classifying said image as belonging to one of said semantic categories if all of the required features and at least one of the frequently occurring features for that semantic category are present in said image. A database contains image information, where the image information includes at least one of already classified images, network locations of already classified images and documents containing already classified images. The database is searched for images matching an input query, comprising, e.g., an image, text, or both.

60 Claims, 14 Drawing Sheets

OTHER PUBLICATIONS

Korn et al., "Fast and Effective Similarity Search In Medical Tumor Databases Using Morphology" IEEE Trans. On Knowledge and Data Engineering vol. 10, No. 6, pp. 889-904, 1998.

Liu et al., "Classification Driven Semantic Based Medical Image Indexing and Retrieval" Tech. Report CMU-RI-TR-98-25, Robotics Institute, Carnegie Mellon University, 1998.

Naphade et al., "A Probabilistic Framework for Semantic Indexing and Retrieval in Video" IEEE Transactions on Multimedia, vol. 3, No. 1. pp. 141-151, Mar. 2001.

Petland et al., "Photobook: Content-Based Manipulation of Image Databases", M.I.T. Media Lab. Perceptual Computing Tech. Report No. 255, Nov. 1993.

Comaniciu et al., "Shape-Based Image Indexing and Retrieval for Diagnostic Pathology", Proc. 14th Int. Conference on Pattern Recognition, Brisbane, Aug. 1998.

Shyu et al., "Assert: A Physician-in-the-loop Content-Based Retrieval System for HRCT Image Databases", Comp. Vision and Image Underst., 75(1/2), pp. 111-132, 1999.

Sclaroff et al., "ImageRover: A Content-Based Image Browser for the World Wide Web", IEEE Workshop on Content-based Access of Image and Video Libraries, Jun. 1997.

Helfman, "Mandela: Architecture for Using Images to Access and Organize Web Information".

Chen et al., "Multi-Modal Browsing of Images in Web Documents", SPIE Document Recognition and Retrieval 1999.

Santini et al., "Emergent Semantics Through Interaction in Image Databases", IEEE Transaction of Knowledge and Data Engineering, Circa Summer 2001.

Minka, "An Image Database Browser tat Learns From user Interaction", MIT Media Laboratory Technical Report #365, 1996.

* cited by examiner

SYSTEM AND METHOD FOR MEASURING IMAGE SIMILARITY BASED ON SEMANTIC MEANING

TECHNICAL FIELD

These teachings relate generally to database management methodologies and, more specifically, the teachings in accordance with this invention relate to methods and apparatus for managing and operating with a database that contains a set of digitally represented images.

BACKGROUND

The flexible retrieval from, manipulation of, and navigation through image databases has become an important problem in the database management arts, as it has applications in video editing, photo-journalism, art, fashion, cataloguing, retailing, interactive computer aided design (CAD), geographic data processing and so forth.

An early content-based retrieval (CBR) system is one known as ART MUSEUM. Reference in this regard can be made to K. Hirata and T. Katzo, "Query by visual example, content based image retrieval", in *Advances in Database Technology—EDBT'92*, A. Pirotte, C. Delobel, and G. Gottlob, Eds., Lecture Notes in Computer Science, vol. 580, 1992. In this particular CBR the retrieval of image data is based entirely on edge features. An early commercial content-based image search engine that had profound effects on later systems was one known as QBIC. Reference in this regard can be had to W. Niblack, R. Berber, W. Equitz, M. Flickner, E. Glasman, D. Petkovic, and P. Yanker, "The QBIC project: Querying images by content using color, texture and shape", in *Proc. SPIE Storage and Retrieval for Image and Video Data Bases*, pp. 172–187, 1994. For color representation this system uses a k-element histogram and average of (R,G,B), (Y,i,q), and (L,a,b) coordinates, whereas for the description of texture it implements the feature set of Tamura (see H. Tamura, S. Mori, and T. Yamawaki, "Textural features corresponding to visual perception", *IEEE Transactions Systems, Man and Cybernetics*, vol. 8, pp. 460–473, 1982.) In a similar fashion, color, texture and shape are supported as a set of interactive tools for browsing and searching images in the Photobook system developed at the MIT Media Lab, as described by A. Pentland, R. W. Picard, and S. Sclaroff, "Photobook: Content-based manipulation of image databases", *International Journal of Computer Vision*, vol. 18, no. 3, pp. 233–254, 1996. In addition to these elementary features, systems such as VisualSeek (see J. R. Smith, and S. Chang, "VisualSeek: A fully automated content-based query system", in *Proc. ACM Multimedia 96*, pp. 87–98, 1996), Netra (see W. Y. Ma, and B. S. Manjunath, "Netra: A toolbox for navigating large image databases" in *Proc. IEEE Int. Conf. on Image Processing*, vol. I, pp. 568–571, 1997) and Virage (see A. Gupta, and R. Jain, "Visual information retrieval", *Communications of the ACM*, vol. 40, no. 5, pp. 70–79, 1997) support queries based on spatial relationships and color layout. Moreover, in the Virage system, users can select a combination of implemented features by adjusting weights according to their own "perception". This paradigm is also supported in the RetrievalWare search engine (see J. Dowe "Content based retrieval in multimedia imaging", in *Proc. SPIE Storage and Retrieval for Image and Video Databases*, 1993.) A different approach to similarity modeling is proposed in the MARS system, as described by Y. Rui, T. S. Huang, and S. Mehrotra, "Content-based image retrieval with relevance feed-back in Mars", in *Proc. IEEE Conf. on Image Processing*, vol. II, pp. 815–818, 1997. In the MARS system the main focus is not on finding a best representation, but rather on the use of relevance feedback to dynamically adapt multiple visual features to different applications and different users.

High-level semantic concepts play a large role in the way that humans perceive images and measure their similarity. Unfortunately, these concepts are not directly related to image attributes. Although many sophisticated algorithms have been devised to describe color, shape and texture features, as was made apparent above, these algorithms do not adequately model image semantics and thus are inherently limited when dealing with broad-content image databases. Yet, due to their computational efficiency, the low-level visual attributes are widely used by content-based retrieval and image navigation systems, leaving the user with the task of bridging the gap between the low-level nature of these primitives and the high-level semantics used to judge image similarity.

Apart from a few exceptions, most conventional image and video retrieval systems neglect the semantic content, and support the paradigm of query by example using similarity in low-level features, such as color, layout, texture, shape, etc. Traditional text-based query, describing the semantic content of an image, has motivated recent research in human perception, semantic image retrieval and video indexing.

In image retrieval the problem of semantic modeling was primarily identified as a scene recognition/object detection task. One system of this type is known as IRIS, see T. Hermes, et al., "Image retrieval for information systems", in *Storage and Retrieval for Image and Video Databases III*, Proc SPIE 2420, 394–405, 1995, which uses color, texture, regional and spatial information to derive the most likely interpretation of a scene and to generate text descriptors, which can be input to any text retrieval system. Another approach in capturing the semantic meaning of the query image is represented by techniques that allow a system to learn associations between semantic concepts and primitive features from user feedback. An early example of this type of system was "FourEyes", as described by T. Minka, "An image database browser that learns from user interaction", *MIT Media Laboratory Technical Report #365*, 1996. This system asks the user to annotate selected regions of an image, and then proceeds to apply the same semantic labels to areas with similar characteristics. This approach was also taken by Chang et al., who introduced the concept of a semantic visual template (S. F. Chang, W. Chen, and H. Sundaram, "Semantic visual templates: linking visual features to semantics", in *Proc. IEEE International Conference on Image Processing*, Chicago, Ill., pp. 531–535, 1995.) In the approach of Chang et al. the user is asked to identify a possible range of color, texture, shape or motion parameters to express the user's query, and the query is then refined using the relevance feedback technique. When the user is satisfied, the query is given a semantic label and stored in a database for later use. Over time, this query database becomes a "visual thesaurus" linking each semantic concept to the range of primitive image features most likely to retrieve relevant items. In video indexing and retrieval, recent attempts to introduce semantic concepts include those described by M. Naphade, and T. Huang, "Probabilistic framework for semantic video indexing, filtering and retrieval", *IEEE Transactions on Multimedia*, vol. 3, no. 1, pp. 141–151, March 2001, and by A. M. Ferman, and M.

Tekalp, "Probabilistic analysis and extraction of video content", in *Proc. IEEE Int. Conf. Image Processing,* Kobe, Japan, October 1999.

The goal of these systems is to overcome the limitations of traditional image descriptors in capturing the semantics of images. By introducing some form of relevance feedback, these systems provide the user with a tool for dynamically constructing semantic filters. However, the ability of these matched filters to capture the semantic content depends entirely on the quality of the images, the willingness of the user to cooperate, and the degree to which the process converges to a satisfactory semantic descriptor.

Content-based retrieval (CBR) methods in medical databases have been designed to support specific tasks, such as retrieval of digital mammograms or 3D MRI images. However, these methods cannot be transferred to other medical applications since different imaging modalities require different types of processing. To enable content-based queries in diverse collections of medical images, the retrieval system must be familiar with the current image class prior to the query processing.

More specifically, medical information systems with advanced browsing capabilities play an increasingly important role in medical training, research, and diagnostics. Thus far, however, the utilization of online medical data has been limited by a lack of effective search methods, and text-based searches have been the dominant approach for medical database management. Since images represent an essential component of the diagnosis, follow-up and research, it is very desirable to use medical images to support browsing and querying of medical databases. Existing CBIR systems depend on visual attributes, such as color, texture and shape, to classify and search for similar images. While this approach may provide satisfactory results when constrained to a single application domain, the use of color, texture and shape features alone do not adequately model image semantics and thus have many limitations when applied to broad content image databases. This problem becomes even more apparent when dealing with semantics of medical images. For this reason, CBIR methods in medical applications have been designed to support specific medical tasks, such as retrieval of tumor shapes in mammograms (see P. Korn, N. Sidiropoulos, C. Faloutsos, E. Siegel, and Z. Protopapas, "Fast and effective retrieval of medical tumor shapes", *IEEE Trans. on Knowledge and Data Engineering,* vol. 10, no. 6, pp. 889–904, 1998), computed tomographies of the lung (see C. R. Shyu, C. E. Brodley, A. C. Kak, A. Kosaka, A. M. Aisen, and L. S. Broderick, "ASSERT: A physician-in-the-loop content based retrieval system for HRCT image databases", *Comp. Vision and Image Underst.,* 75(1/2), pp. 111–132, 1999), 3D MRI images in neurology (see J. Declerck, G. Subsol, J-P. Thirion, and N. Ayache, "Automatic retrieval of anatomical structures in 3D medical images", *Tech. Report* 2485, INRIA, Sophia-Antipolis, France, 1995; A. Guimond, and G. Subsol, "Automatic MRI database exploration and applications", *Pattern Recognition and Artificial Intelligence,* vol. 11, no. 8, December 1997; Y. Liu, F. Dellaert, and W. E. Rothfus, "Classification Driven Semantic Based Medical Image Indexing and Retrieval", *Tech. Report* CMU-RI-TR-98-25, Robotics Institute, Carnegie Mellon University, 1998), or pathology (see D. Comaniciu, D. Foran, and P. Meer, "Shape-based image indexing and retrieval for diagnostic pathology", *Proc.* 14$^{th}$ *Int. Conference on Pattern Recognition,* Brisbane, August 1998.) However, these methods are task-specific and cannot be transferred to other medical applications since different imaging modalities require different processing methods.

Therefore, to enable content-based queries for research and diagnostic purposes, the information retrieval system must be familiar with the current image class prior to the query processing. Hence, for this to occur the categorization of medical images into different imaging modalities is required to support further queries. This need has not been adequately addressed prior to this invention.

As maybe appreciated, these shortcomings are not limited only to medical image databases and, therefore, there is a long-felt and unfulfilled need to provide an improved technique that automatically characterizes images according to their modalities, and that also employs semantic information for browsing, searching, querying and visualizing collections of digital images.

SUMMARY OF THE PREFERRED EMBODIMENTS

The foregoing and other problems are overcome, and other advantages are realized, in accordance with the presently preferred embodiments of these teachings.

Described herein is technique for the automatic categorization of images according to their semantic meanings. In a presently preferred, but not limiting embodiment, the images are medical images. A semantically based set of visual features is described, as is their relevance and organization for capturing the semantics of different imaging modalities. The features are used in conjunction with a categorization metric for enabling an intelligent annotation, browsing and searching of medical databases. An algorithm provides basic semantic knowledge about the image, and may serve as a front-end to domain specific medical image analysis methods. An aspect of these teachings is in providing an Internet portal for enabling users to browse and query online medical databases. It is shown that accurate categorization can be achieved by exploiting the important visual properties of each modality.

A computer implemented method is disclosed for characterizing, annotating and determining image similarity based on semantic meaning of images. The method includes deriving a plurality of semantic categories for representing important semantic cues in images, where each semantic category is modeled through a combination of perceptual features that define the semantics of that category and that discriminate that category from other categories; for each semantic category, forming a set of the perceptual features comprising required features and frequently occurring features; comparing an image to said semantic categories; and classifying said image as belonging to one of said semantic categories if all of the required features and at least one of the frequently occurring features for that semantic category are present in said image.

A database stores image information, where the image information includes at least one of already classified images, network locations of already classified images and documents containing classified images. The database is searched for images matching an input query.

For example, the image information includes, in one embodiment, web URLs, or pointers to database entries of same, of already classified digital images, as well as locations of documents related to the digital images. As an example, for a parent document there may be links both to and from a digital image contained within the document. The database is searched to locate images matching an input query. The query can include an image, or text specifying a search topic or category, and may further include a semantic query. A combination of image and text data can also be used as a query.

Note that the database may not contain any images at all, but may instead contain digital image classification information and the network addresses of digital images and documents containing the digital images. In general the database contains pointers to externally stored, pre-classified digital images and related documents. The database itself may be local or remote, and it could be distributed over a plurality of locations.

The images stored in or referenced by the database may be obtained at least in part through the Internet, such as by the activity of an automated web crawler. In one embodiment the images are medical images, and the database maybe searched for at least one image that satisfies thresholds established by a search query. The database may be remotely located and accessed through the Internet via a server. In one embodiment an image query to the database server can be made in conjunction with a text-based search algorithm executed by the server to retrieve a multi-media object from or through the database.

The method includes segmenting an input image by employing texture segmentation, color segmentation and foreground/background segmentation, where texture segmentation includes forming a texture map and where color segmentation includes forming a region map. The foreground/background segmentation includes using the texture map and the region map to determine if there is at least one dominant object in the image, and to form an object map. The input image, texture map, region map and object map are further processed to compute for each region in the region map, and for each object in the object map, a set of local features that may include, but need not be limited to, size, boundary, neighbors, boundary curvature, texture, mean color, color name, and shape properties for each region/object.

The local features are analyzed to compute regional features, indicating a presence of semantic cues such as at least one of skin, sky, grass, snow, nature, water, man-made objects, man-made blobs, flowers and texture. The local features are combined to compute global features that describe a global appearance of the image. The global features can include at least one of the number of details, histogram of color names, description of color composition, number of regions, number of blobs, number of objects, number of straight lines, number of regular curves, energy, spatial activity, symmetry and measures of contrast.

The end result is a set of image metadata that is suitable for use in searching for and identifying stored images, such as during an image search or query procedure that is performed over a data communications network.

Also described is method for searching the Internet. The method includes providing at least one server accessible by a plurality of clients; downloading a program to a client, the program including an Internet searching program operable for locating at least one type of data; and executing the downloaded program on the client, and returning to the server URLs corresponding to located data. In a preferred, but not limiting embodiment, the at least one type of data comprises image data.

Also described is a system for obtaining information from the Internet. The system includes at least one server accessible by a plurality of clients. The server is operable for downloading a program to a client, where the program includes an Internet searching program operable for locating at least one type of data. The downloaded program is executable by the client and returns to the server URLs corresponding to located data. The server further includes a database, searchable by the clients, for storing information corresponding to information returned by the downloaded program.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein.

DETAILED DESCRIPTION OF THE PREFERRED EMBODIMENTS

The teachings of this invention are related to some extent to the subject matter described in copending U.S. patent application Ser. No. 10/033,597, filed Dec. 27, 2001, entitled "Perceptual Method for Browsing, Searching, Querying and Visualizing Collections of Digital Images", by Aleksandra Mojsilovic and Bernice E. Rogowitz, incorporated by reference herein in its entirety. Prior to describing the teachings of this invention, it will be instructive to review the teachings of the commonly assigned U.S. patent application Ser. No. 10/033,597.

In brief, that invention provides an image processing method and system that is based on human perception, and that extracts semantic information about images. The method allows images to be organized and categorized by semantic content, without requiring key words. The method can enable the development of perceptual front-ends to many image applications. The method is implemented using a set of image processing algorithms that extract visual attributes from images and analyzes them to assign semantic meaning.

A first method assigns semantic meaning to an image, without requiring the use of a costly and labor-intensive step where each image is labeled manually with a key word. A second method enables a user to search, navigate, and browse through a library of images based on semantic categories. These are important advantages when developing user-interfaces, and when developing useful multimedia databases.

Figure 1:
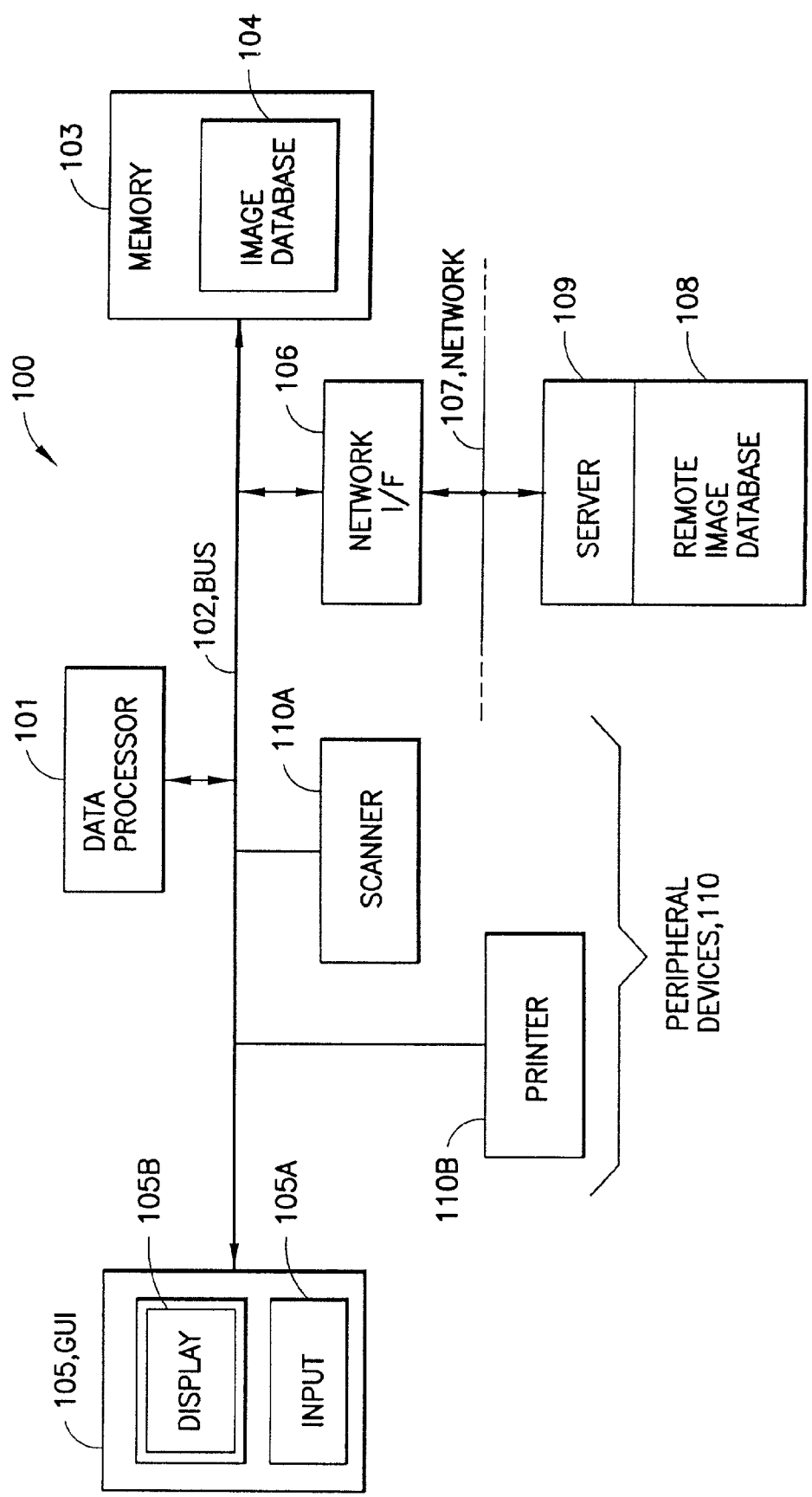
FIG. 1 is simplified block diagram of a data processing system that is suitable for practicing this invention.

FIG. 1 is a simplified block diagram of a data processing system 100 that is suitable for practicing that invention, as well as the teachings of the present invention. The data processing system 100 includes at least one data processor 101 coupled to a bus 102 through which the data processor 101 may address a memory sub-system 103, also referred to herein simply as the memory 103. The memory 103 may include RAM, ROM and fixed and removable disks and/or tape. The memory 103 is assumed to store a program containing program instructions for causing the data processor 101 to execute methods in accordance with the teachings of the invention. Also stored in the memory 103 can be at least one database 104 containing digital image data and/or references or pointers to externally stored digital images, image classification information and also document data. The image data may be separate from the document data and/or the image data may comprise a portion of the document data. For example, some portion of the database 104 may store scientific publications containing digital images, or it may store links to these publications, such as network addresses including URLs. The digital image data may include photographs obtained from a digital camera, and/or photographs that are obtained from a conventional film camera and then scanned into the memory 103, and/or computer generated images, and/or artworks that are photographed and scanned into the memory 103. In general, the digital image data may be any desired type or types of images, including digitally stored images of persons, places, abstract forms, drawings, paintings, photographs of sculptures, photographs of microscopic subjects, etc.

The data processor 101 is also coupled through the bus 102 to a user interface, preferably a graphical user interface (GUI) 105 that includes a user input device 105A, such as one or more of a keyboard, a mouse, a trackball, a voice recognition interface, as well as a user display device 105B, such as a high resolution graphical CRT display terminal, a LCD display terminal, or any suitable display device.

The data processor 101 may also be coupled through the bus 102 to a network interface 106 that provides bidirectional access to a data communications network 107, such as an intranet and/or the internet. Coupled to the network 107 can be one or more sources and/or repositories of digital images, such as a remote digital image database 108 reachable through an associated server 109. As will be described below, the digital image database may include a medical database, and the server 109 may include an Internet portal providing access to the medical database. This example of the use of medical images is not to be construed in any way as being a limitation upon the practice of this invention.

The data processor 101 is also preferably coupled through the bus 102 to at least one peripheral device 110, such as a scanner 110A and/or a printer 110B.

In general, these teachings may be implemented using one or more software programs running on a personal computer, a server, a microcomputer, a mainframe computer, a portable computer, and embedded computer, or by any suitable type of programmable data processor 101. The use of this invention substantially improves the analysis, description, annotation and other information processing tasks related to digital images. The teachings of this invention can also be configured to provide real-time processing of image information. The methods may be used to process the digital image data stored in or referenced by the database 104 or, as will be noted below, in the remotely stored database 108 over the network 107 and in cooperation with the server 109.

Figure 2:
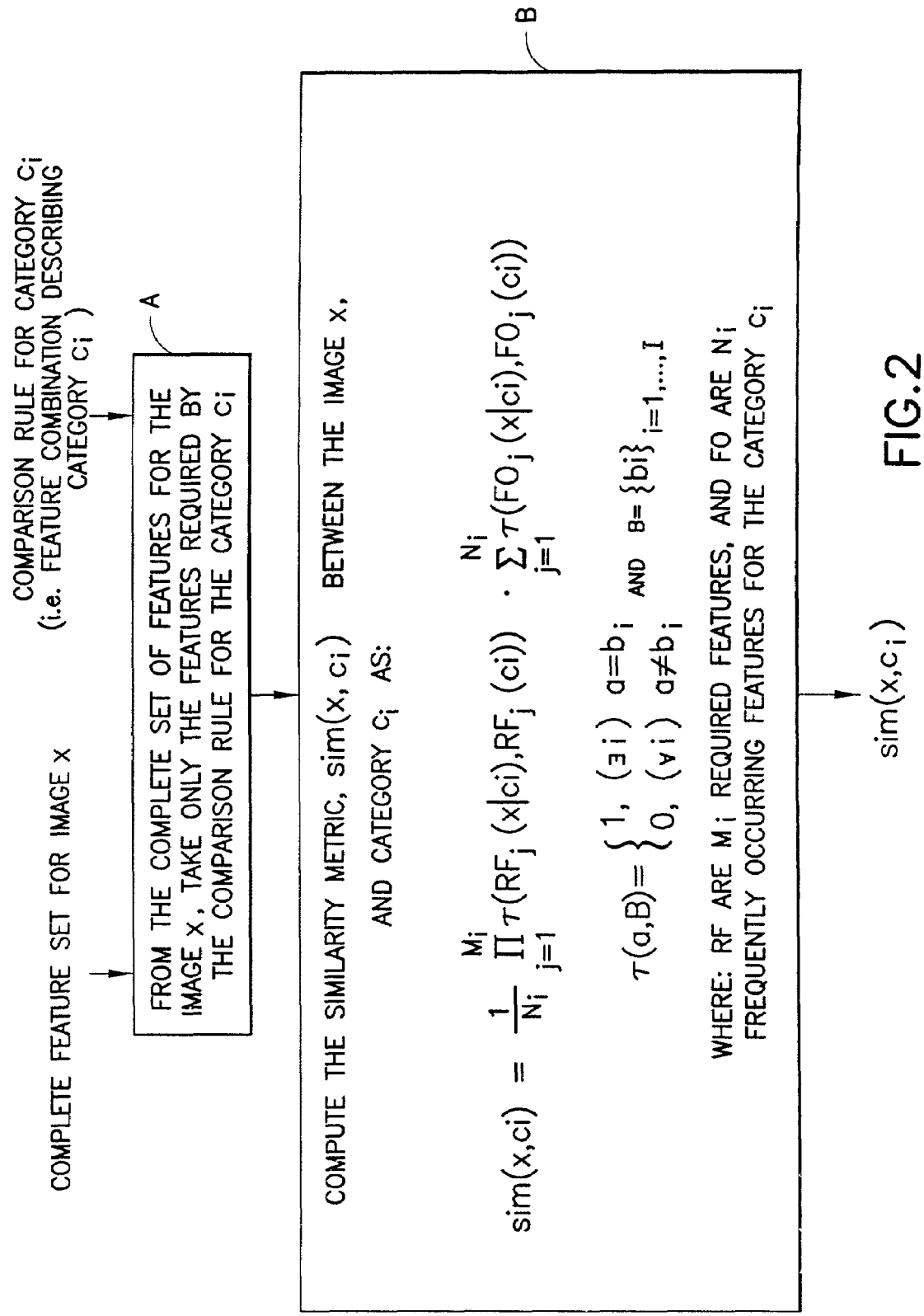
FIG. 2 is a logic flow diagram that illustrates a method for computing a similarity metric between an image x and a semantic category $c_i$.

By way of introduction, FIG. 2 is a logic flow diagram that illustrates a method for computing a similarity metric (sim(x,$c_i$)) between an image x and a semantic category $c_i$. The method is assumed to be executed by the data processor 101 under control of a program or programs stored in the memory 103. The image x is assumed to be an image stored in the database 104. Step A takes as inputs a complete feature set (CFS) for the image x, and a comparison rule for the category $c_i$, that is, a feature combination that describes category $c_i$. At Step A the method selects from the CFS of image x only those features required by the comparison rule for category $c_i$. At Step B the method computes the similarity metric sim(x, $c_i$) in accordance with the illustrated mathematical expression.

Figure 3:
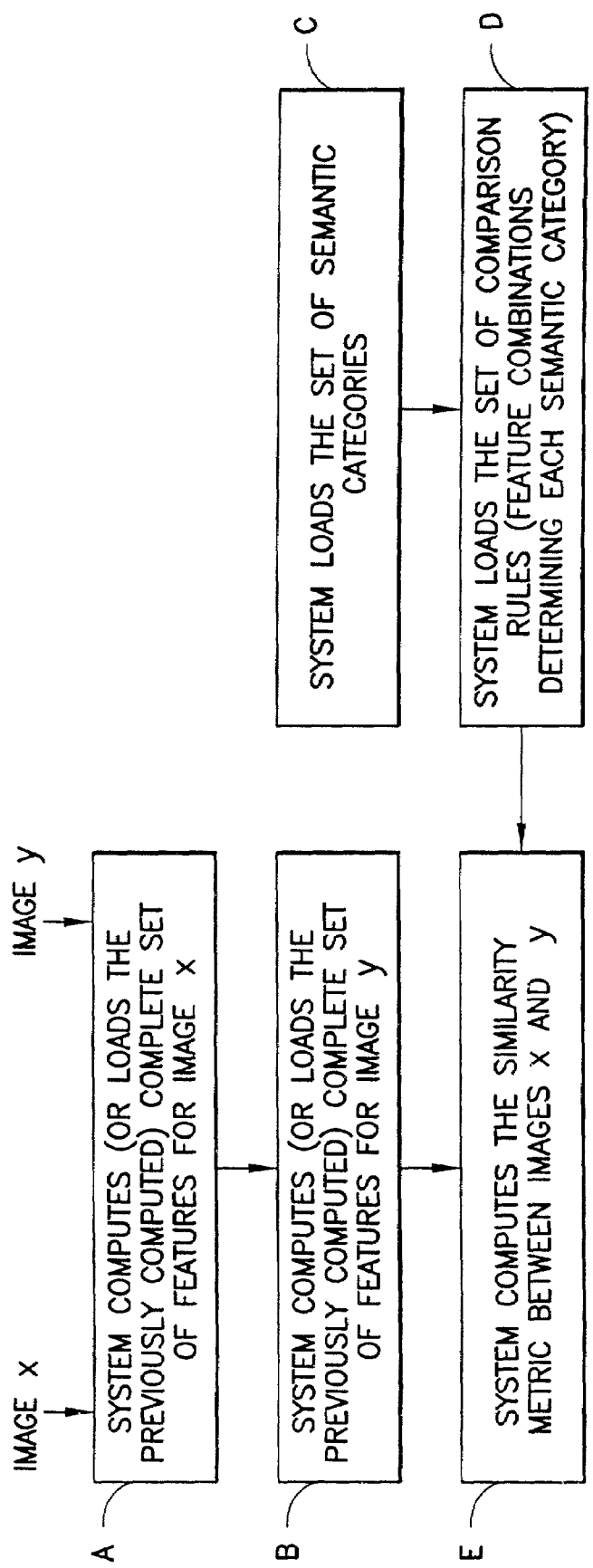
FIG. 3 is a logic flow diagram that illustrates a method for measuring image similarity based on semantic categorization.

FIG. 3 is a logic flow diagram that illustrates a method for measuring image similarity based on semantic categorization. Step A receives as inputs two images, i.e., images x and y, and computes, or loads a previously computed CFS for image x. At Step B the data processing system 100 computes, or loads a previously computed CFS for image y. On a separate path, at Step C the data processing system 100 loads a set of semantic categories, and at Step D the data processing system 100 loads a set of comparison rules, i.e., feature combinations that determine each semantic category. Then at Step E, using the previously computed and/or preloaded information from Steps A, B, C and D, the data processing system 100 computes the similarity metric between the images x and y.

Figure 4:
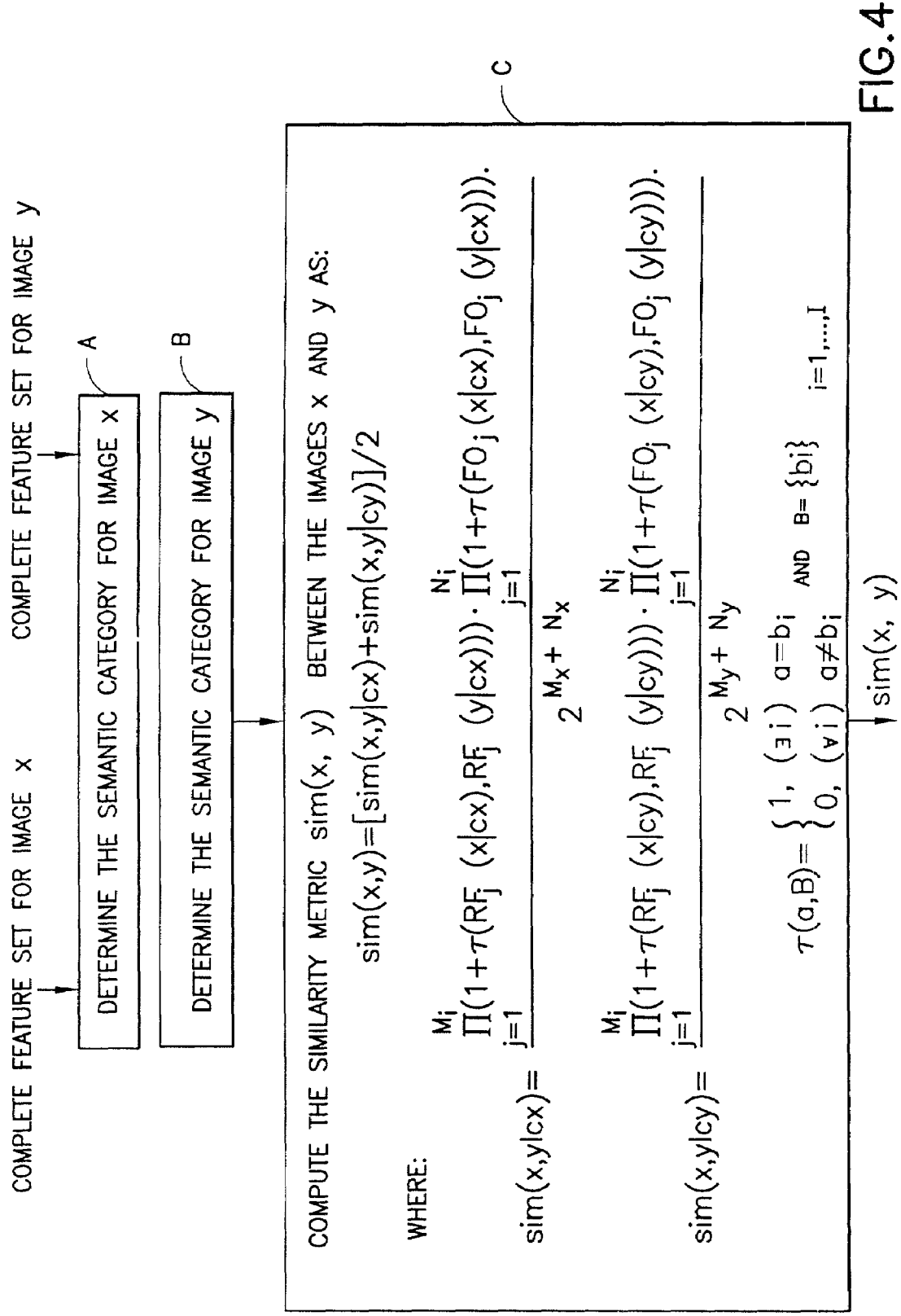
FIG. 4 is a logic flow diagram that illustrates a method for computing a similarity metric between images x and y.

FIG. 4 is another logic flow diagram of the method for computing the similarity metric between the images x and y. Steps A and B correspond to Step C of FIG. 3, while Step C corresponds to Step E of FIG. 3 and shows the mathematical expressions involved in computing the similarity metric sim(x,y), as will be described in further detail below.

Figure 5:
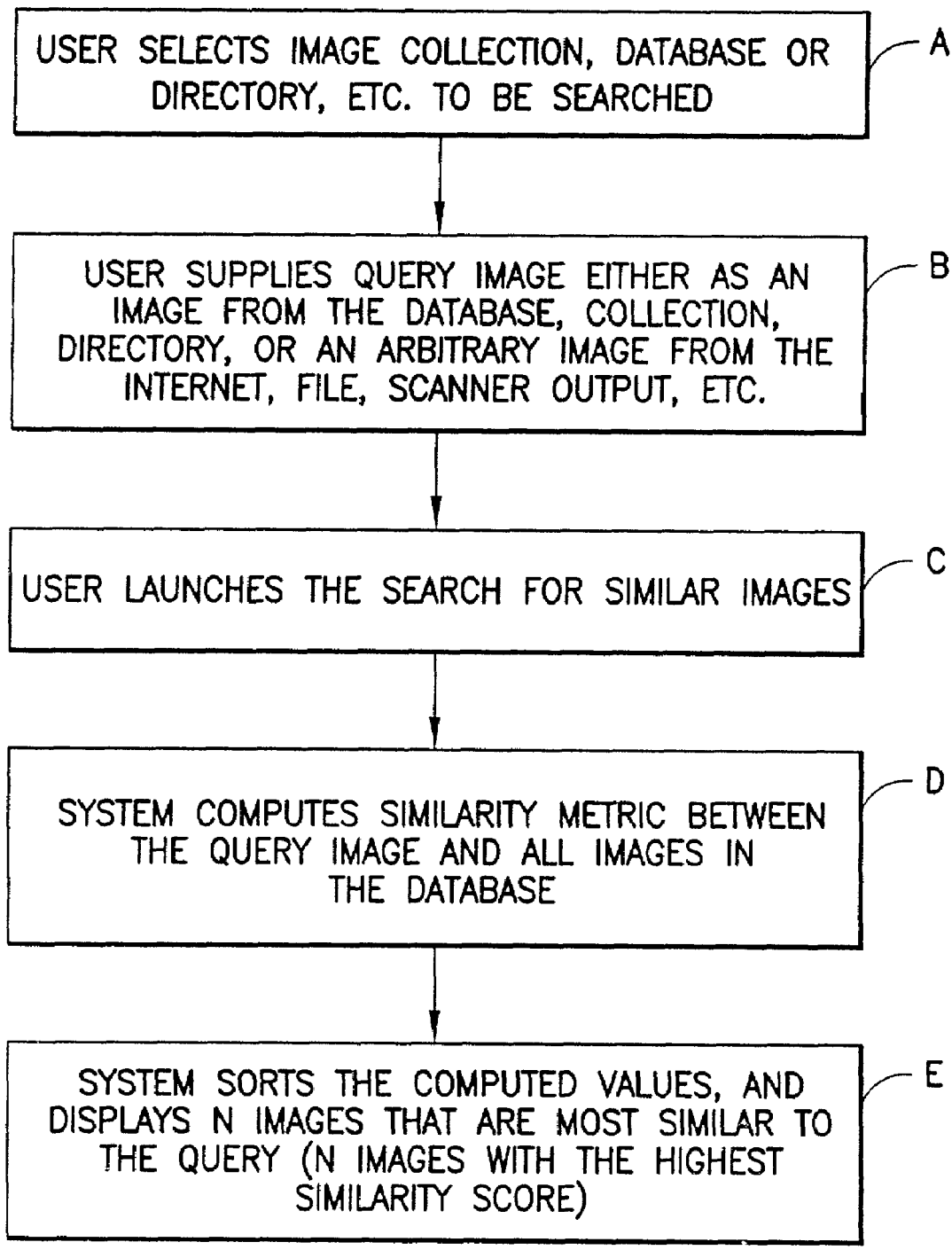
FIG. 5 is a logic flow diagram that illustrates a method for performing a database search based on semantic categorization.

FIG. 5 is a logic flow diagram that illustrates a method for performing a database 104 search based on semantic categorization. At Step A the user interacts with the GUI 105 and selects a set of images to be searched, such as an image collection, the database 104, or a directory of images stored in the memory 103. At Step B the user supplies a query image, such as an image from the database 104, or some other image (for example, an image from the network 107, a file, the output of the scanner 110A, or from any other suitable source.) At Step C the user launches the search for similar images to the query image. At Step D the data processing system 100 computes the similarity metric between the query image and all images in the database 104 (or images referenced by information stored in the database 104). At Step E the data processing system 100 sorts the computed values and displays N images on the user display device 105B. The displayed N images are those selected by the data processing system 100 to be the most similar to the query image, i.e., the N images with the highest computed similarity score. Alternatively, if desired for some reason the user could request the data processing system 100 to display N images that are the most dissimilar to the query image, i.e., the N images with the lowest computed similarity score. The maximum value that N may attain maybe unconstrained, or it may be constrained by the user to some reasonable number (e.g., four, eight or ten).

Figure 6:
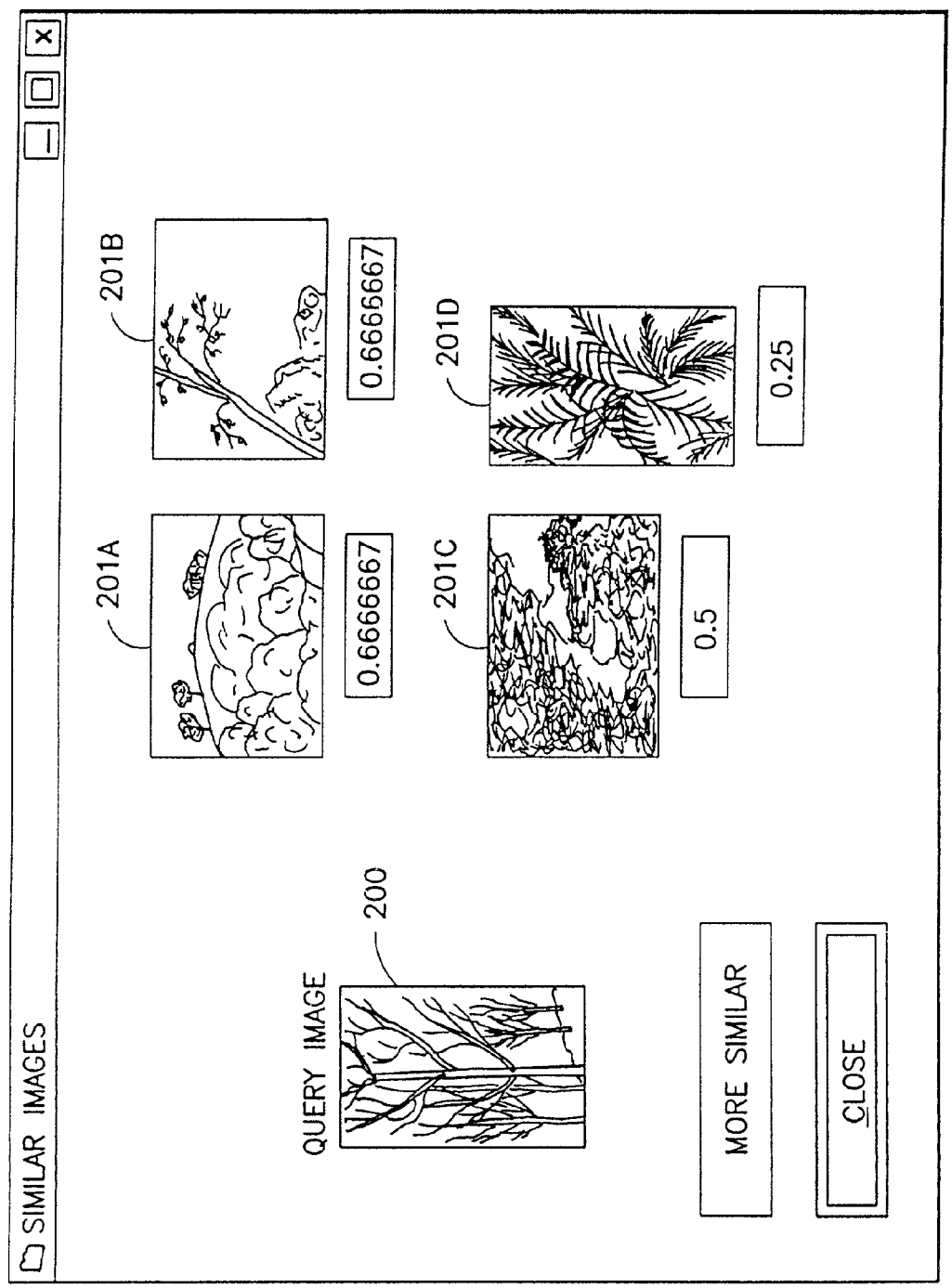
FIG. 6 is an example of the result of a database search.

FIG. 6 is an example of the result of a search of the database 104, and shows the query image 200 (for example, an image of a tree) and the N (e.g., four) images returned by the system 100 as being the most similar to the query image 200, i.e., those images 201A through 201D having the highest computed similarity score in accordance with the method shown in FIGS. 3 and 4. Note that images 201A and 201B happen to have identical similarity scores (0.6667).

Figure 7:
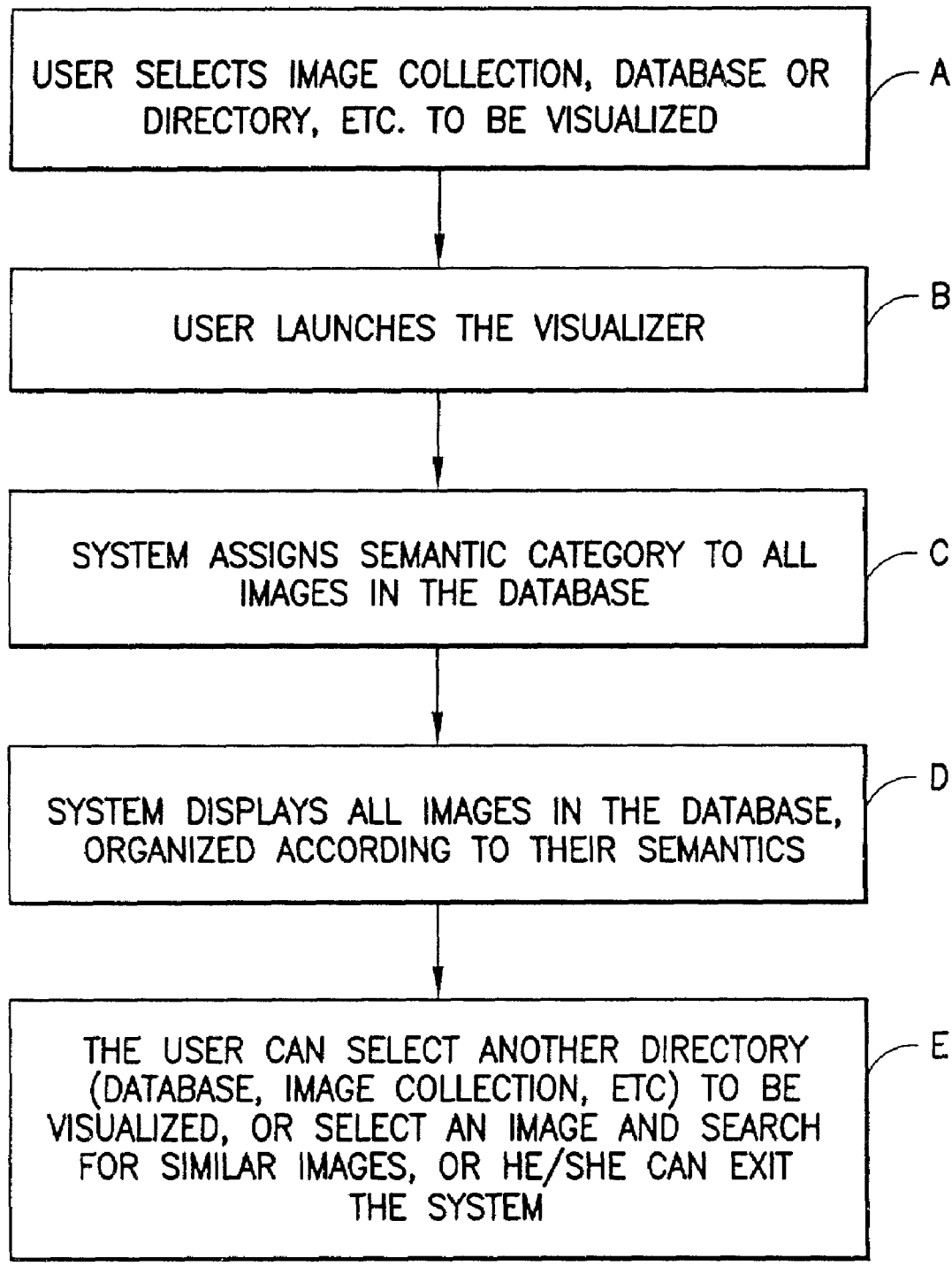
FIG. 7 is a logic flow diagram that illustrates a further method for performing a database search based on semantic categorization.

FIG. 7 is a logic flow diagram that illustrates a further method for performing a database search based on semantic categorization. At Step A the user interacts with the GUI 105 and selects a set of images to be visualized, such as an image collection, the database 104, or a directory of images stored in the memory 103. At Step B the user launches the system visualizer. At Step C the data processing system 100 assigns a semantic category to all images in the database 104. At Step D the data processing system 100 displays all images in the database 104, organized according to their semantics. At Step E the user may select another set of images to be visualized, or the user may select one image and search for similar images, as in the method of FIG. 5, or the user may simply terminate the method.

Figure 8:
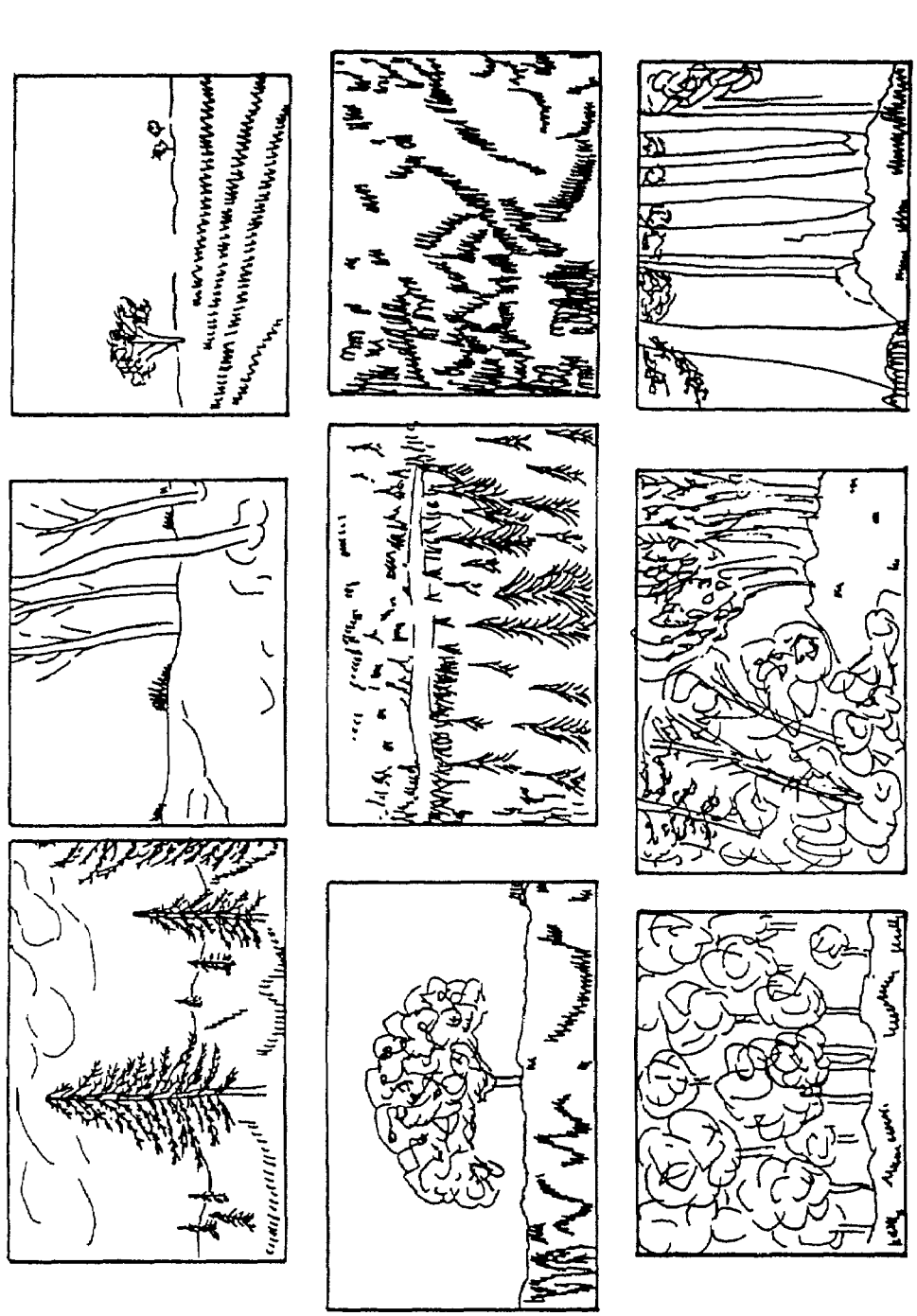
FIG. 8 is an example of database visualization.

FIG. 8 is an example of the result of visualization of the database 104 in accordance with the method of FIG. 7. In this example thumbnail-type images showing trees are grouped according the their semantics. The visualization could also be presented in the form of a storage media directory structure having a listing of image files by folders, etc.

The foregoing system and methods provide for the semantic categorization and retrieval of photographic images based on low-level image descriptors derived preferably from perceptual experiments performed with human observers. In the method multidimensional scaling and hierarchical clustering are used to model the semantic categories into which human observers organize images. Through a series of psychophysical experiments and analyses, the definition of these semantic categories is refined, and the results are used to discover a set of the low-level image features to describe each category. The image similarity metric embodies the results and identifies the semantic category of an image from the database 104, and is used to retrieve the most similar image(s) from the database 104. The results have been found to provide a good match to human performance, and thus validate the use of human judgments to develop semantic descriptors. The methods of this invention can be used for the enhancement of current image/video retrieval methods, to improve the organization of large image/video databases, and in the development of more intuitive navigation schemes, browsing methods and user interfaces.

The methods are based on the results of subjective experiments aimed at: a) developing and refining a set of perceptual categories in the domain of images, such as photographic images, b) deriving a semantic name for each perceptual category, and c) discovering a combination of low-level features which best describe each category. The image similarity metric embodies these experimental results, and may be employed to annotate images or to search the database 104, using the semantic concepts. To analyze the data from the experiments it was preferred to use multidimensional scaling and hierarchical cluster analysis. A brief description of both of these techniques is now provided.

Multidimensional scaling (MDS) is a set of techniques that enables researchers to uncover the hidden structures in data (J. Kruskal, and M. Wish, *Multidimensional scaling*, Sage Publications, London, 1978) MDS is designed to analyze distance-like data called similarity data; that is, data indicating the degree of similarity between two items (stimuli). Traditionally, similarity data is obtained via subjective measurement and arranged into a similarity matrix Δ, where each entry, $\delta_{ij}$, represents similarity between stimuli i and j. The aim of MDS is to place each stimulus from the input set into an n-dimensional stimulus space (the optimal dimensionality of the space, n, should be also determined in the experiment). The coordinates of all stimuli (i.e., the configuration) are stored in a matrix X, also called the group configuration matrix. The points $x_i = [x_{i1}\ x_{i2}\ \ldots\ x_{in}]$ representing each stimulus are obtained so that the Euclidean distances $d_{ij}$ between each pair of points in the obtained configuration match as closely as possible the subjective similarities $\delta_{ij}$ between corresponding pairs of stimuli. The traditional way to describe a desired relationship between the distance $d_{ij}$ and the similarity $\delta_{ij}$ is by the relation d=f(δ), such as (d=f(δ)=aδ+b) where for a given configuration, values a and b must be discovered using numerical optimization. There are many different computational approaches for solving this equation. Once the best f is found, one then searches for the best configuration X of points in the stimulus space. This procedure is repeated for different n's until a further increase in the number of dimensions does not bring a reduction in the following error function (also known as stress formula 1 or Kruskal's stress formula):

$$s^2(\Delta, X, f) = \frac{\sum_i \sum_j [f(\delta_{ij}) - d_{ij}]^2}{\sum_i \sum_j f(\delta_{ij})^2} \quad (1)$$

Once the MDS configuration is obtained the remaining task is interpreting and labeling the dimensions. Usually it is desired to interpret each dimension of the space. However, the number of dimensions does not necessarily reflect all of the relevant characteristics. Also, although a particular feature exists in the stimulus set, it may not contribute strongly enough to become visible as a separate dimension. Therefore, one useful role of MS is to indicate which particular features are important.

Having obtained a similarity matrix, hierarchical cluster analysis (HCA) organizes a set of stimuli into similar units (R. Duda, and P. Hart, *Pattern classification and scene analysis*, John Wiley & Sons, New York, N.Y., 1973.) This method starts from the stimulus set to build a tree. Before the procedure begins, all stimuli are considered as separate clusters, hence there are as many clusters as there are stimuli. The tree is formed by successively joining the most similar pairs of stimuli into new clusters. As the first step, two stimuli are combined into a single cluster. Then, either a third stimulus is added to that cluster, or two other clusters are merged. At every step, either individual stimulus is added to the existing clusters, or two existing clusters are merged. Splitting of clusters is forbidden. The grouping continues until all stimuli are members of a single cluster. There are many possible criteria for deciding how to merge clusters. Some of the simplest methods use a nearest neighbor technique, where the first two objects combined are those that have the smallest distance between them. At every step the distance between two clusters is obtained as the distance between their closest two points. Another commonly used technique is the furthest neighbor technique, where the distance between two clusters is obtained as the distance between their furthest points. The centroid method calculates the distances between two clusters as the distance between their means. Note that, since the merging of clusters at each step depends on the distance measure, different distance measures can result in different clustering solutions for the same clustering method.

Clustering techniques are often used in combination with MDS to clarify the dimensions and interpret the neighborhoods in the MDS configuration. However, similarly to the labeling of the dimensions in the MDS, interpretation of the clusters is usually done subjectively and strongly depends on the quality of the data.

A series of experiments were conducted: 1) an image similarity experiment aimed at developing and refining a set of perceptual categories for photographic image databases, 2) a category naming and description experiment aimed at deriving a semantic name for each category, and a set of low-level features which describe it, and 3) an image categorization experiment to test the results of the metric, derived from the previous experiments, against the judgments of human observers on a new set of photographic images.

All of the images in these experiments were selected from standard CD image collections, and provided high image quality and broad content. The images were selected according to the following criteria. First, a wide range of topics was included: people, nature, buildings, texture, objects, indoor scenes, animals, etc. Following a book designed to teach photography, the images were explicitly selected to include equal proportions of wide-angle, normal, and close-up shots, in both landscape and portrait modes. The selection of images was iterated so that it included images with different levels of brightness and uniform color distribution. Three sets of images (Set 1, Set 2 and Set 3) included 97 images, 99 images and 78 images, respectively. The size of each printed image was approximately 1.5×1 inches (for a landscape), or 1×1.5 inches (for a portrait). All images were printed on white paper using a high-quality color printer.

Seventeen subjects participated in these experiments ranging in age from 24 to 65. All of the subjects had normal or corrected-to-normal vision and normal color vision. The subjects were not familiar with the input images.

In previous work (B. Rogowitz, T. Frese, J. Smith, C. A. Bouman, and E. Kalin, *Perceptual image similarity experiments,* in *Proc. of SPIE,* 1997), two methods were used for measuring the similarity between the 97 images in data set 1, and multidimensional scaling was applied to analyze the resulting similarity matrices. It was found that both psychophysical scaling methods produced very similar results. In particular, both revealed two major axes, one labeled "human vs. non-human" and the other labeled "natural vs. manmade". In both results, it was observed that the images clustered into what appeared to be semantic groupings, but the analysis was not carried further.

As a starting point in determining the basic categories of human similarity judgment, the similarity data from the foregoing journal article (B. Rogowitz et al., *Perceptual image similarity experiments,* in *Proc. of SPIE,* 1997) was used in combination with hierarchical cluster analysis (HCA). It was found that the perceptual distances between the 97 images were indeed organized into clusters. To confirm the stability of the most important clusters in the HCA solution the original data was split in several ways and separate HCAs were performed for each part. As suggested by R. Duda et al., *Pattern classification and scene analysis,* some of the stimuli was eliminated from the data matrix and the HCA was applied to the remaining stimuli. The clusters that remained stable for various solutions were referred to as initial categories (IC) or as "candidate" clusters. An excellent correspondence was observed between the neighborhoods in the MDS configuration and the clusters determined by the HCA. It was also observed that some of the 97 images did not cluster with other images. Rather than force them to be organized into more populous clusters, they were treated as separate, individual clusters.

A purpose to a first experiment, Experiment 1: Similarity Judgments for Image Set 2 to derive the Final Set of Semantic Categories, was to collect a second set of similarity judgments which enabled: 1) examining the perceptual validity and reliability of the categories identified by the hierarchical cluster analysis, 2) developing a final set of categories based on the similarity data for Set 1 and Set 2, and 3) establishing the connections between the categories.

For this experiment, 97 thumbnails of all the images in Set 1 were printed, organized by cluster, and fixed to a tabletop, according to their initial categories, IC. The images were organized with a clear spatial gap between the different categories. Also printed were thumbnails of images from Set 2 (the new set). Twelve subjects (7 male and 5 female) participated in this experiment. Subjects were asked to assign each image from Set 2 into one of the initial categories, placing them onto the tabletop so that the most similar images were near each other. No instructions were given concerning the characteristics on which the similarity judgments were to be made, since this was the very information that the experiment was designed to uncover. The order of the stimuli in Set 2 was random and different for each subject. This was done to counterbalance any effect the ordering of the stimuli might have on the subjective judgments. The subjects were not allowed to change the initial categories, as these images were fixed to the tabletop and could not be moved. However, subjects were allowed to do whatever they wished with the new images. They were free to change their assignments during the experiment, move images from one category into another, keep them on the side and decide later, or to start their own categories. Finally, at the end of the experiment, the subjects were asked to explain some of their decisions (as will be described later, these explanations, as well as the relative placement of images within the categories, were valuable in data analysis).

The first step in the data analysis was to compute the similarity matrix for the images from Set 2. The matrix entry represents a number of times images i and j occur in the same category. Multidimensional scaling was then used to analyze this similarity matrix. Note, that in this case matrix elements represent similarities. Since MDS methods are based on the idea that the scores are proportional to distances, it was desirable to preprocess the collected data according to the following relation:

$$\text{dissimilarity} = NS - \text{similarity}. \tag{2}$$

where NS is number of subjects in the experiments.

A further step in the data analysis was to test the stability of the initial categories and further refine them. To do so, the similarity matrix $\Delta_{S_2,IC}$ for the images from Set 2 and the initial categories IC. The matrix entry $\Delta_{S_2,IC}(i,j)$ is computed in the following way:

$$\Delta_{S_2,IC}(i,j) = \begin{cases} \Delta' = \text{number of times images } i \text{ and} & i, j \in \text{Set 2} \\ \quad j \text{ occured in the same category,} \\ \Delta'' = \text{number of times image } i & i \in \text{Set 2 and } j \in IC \\ \quad \text{occured in the category } j, \\ \Delta''' = d(i,j) & i, j \in IC \end{cases} \quad (3)$$

where d(i,j) is the Euclidean distance between the centroids of the initial clusters normalized to occupy the same range of values as similarity measures $\Delta'$ and $\Delta''$.

Once the similarity matrix is computed hierarchical cluster analysis was applied to determine the final set of semantic categories (FC), which now included 196 images. A first supercluster that emerged from the experiments represented images of people, followed by the clusters with images of man-made objects and man-made environments. The remaining images were further subdivided into natural scenes and natural objects (pictures of animals, plants, etc.). These findings confirmed the multidimensional scaling results on the first set of images. Similar to the division in the 2D MDS configuration, four major image categories are present: 1) humans, 2) man-made, 3) natural scenes and 4) natural objects. Finally, as in the 2D MDS configuration, textures were seen as an isolated category. However, it should be noted that in this experiment they were placed closer to the clusters from nature, mainly because the texture images in the image sets were dominated by natural textures as opposed to human-made textures.

Figure 9:
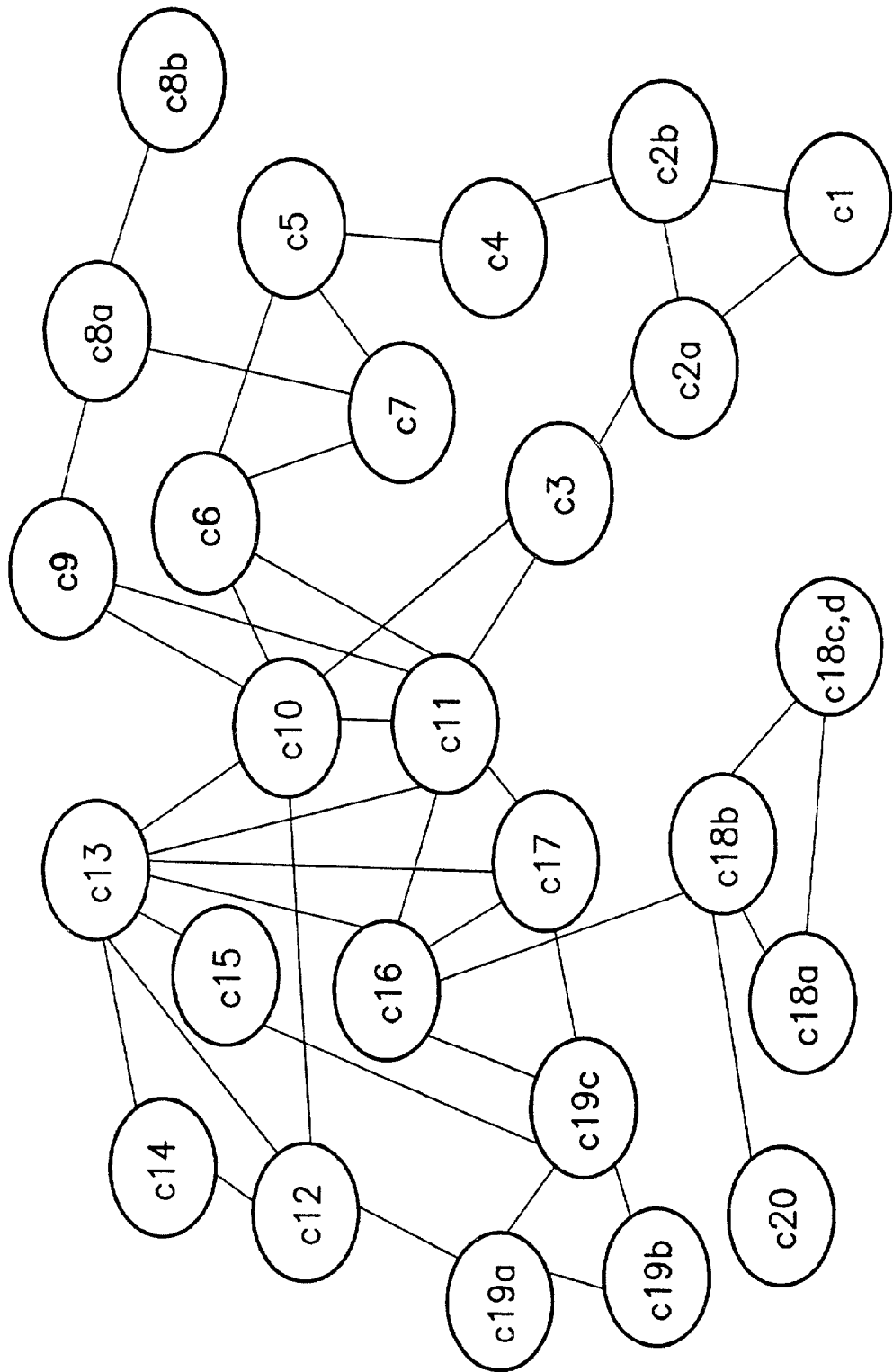
FIG. 9 is a graph that shows connections and transitions between a plurality of image categories.

A next step in the data analysis was to develop a measure of the distance between categories, and their connections. To do so, the similarity data was transformed into the confusion matrix CM, where each entry CM(i,j) represents the average number of images from category $c_i$ placed into category $c_j$ (and vice versa). Together with the comments from the subjects, these values were used to investigate the relationships and establish transitions between the categories. Moreover, since the HCA technique expresses the structure and groupings in the similarity matrix hierarchically, the clustering results were also helpful in this task. As a result, the graph of FIG. 9 was constructed for showing the connections and the transitions between the categories. Each category was represented as a node in the graph. Two nodes are connected if the corresponding categories had the confusion ratio above defined threshold.

After the final categories had been identified, another experiment was performed to determine whether these algorithmically-derived categories were semantically distinct. In this experiment, observers were requested to give names to the final categories identified in the first experiment. To further delineate the categories, and to identify high-level image features that discriminate the categories perceptually, the observers were also requested to provide descriptors for each of the categories. Each subject was asked to name each category and to write a brief description and main properties of the category. This experiment was helpful in many different ways. First, it was used to test the robustness of the categories and test whether people see them in a consistent manner. Furthermore, the experiment helped in establishing if the determined categories are semantically relevant. And finally, the written explanations are valuable in determining pictorial features that best capture the semantics of each category.

A non-exhaustive listing of categories and their semantics are as follows.

C1: Portraits and close-ups of people. A common attribute for all images in this group is a dominant human face.

C2a: People outdoors. Images of people, mainly taken outdoors from medium viewing distance.

C2b: People indoors. Images of people, mainly taken indoors from medium viewing distance.

C3: Outdoor scenes with people. Images of people taken from large viewing distance. People are shown in the outdoor environment, and are quite small relative to image.

C4: Crowds of people. Images showing large groups of people on a complex background.

C5: Cityscapes. Images of urban life, with typical high spatial frequencies and strong angular patterns.

C6: Outdoor architecture. Images of buildings, bridges, architectural details that stand on their own (as opposed to being in a cityscape).

C7: Techno-scenes. Many subjects identified this category as a transition from C5 to C6.

C8a: Objects indoors. Images of man-made object indoors, as a central theme.

Other categories included: waterscapes with human influence, landscapes with human influence, waterscapes, landscapes with mountains, images where a mountain is a primary feature, sky/clouds, winter and snow, green landscapes and greenery, plants (including flowers, fruits and vegetables), animals and wildlife, as well as textures, patterns and close-ups.

Although the individual subjects used different verbal descriptors to characterize the different categories, there were many consistent trends. It was found that certain objects in an image had a dominating influence. In the nature categories by example, and for all human subjects, water, sky/clouds, snow and mountains emerged as very important cues. Furthermore, these were often strongly related to each other, determining the organization and links between the groups. The same was found to be true for images with people, as the observers were very sensitive to the presence of people in the image, even if the image is one of a natural scene, an object, or a man-made structure. Color composition and color features were also found to play an important role in comparing natural scenes. On the other hand, color was found to be rarely used by the human observers when describing images with people, man-made objects and environments. Within these categories, however, spatial organization, spatial frequency and shape features were found to mainly influence similarity judgments. Furthermore, with the exception of flowers, fruits and exotic animals, strong hues (such as bright red, yellow, lime green, pink, etc.) are not generally found in natural scenes. Therefore, these colors in combination with the spatial properties, shape features or overall color composition indicate the presence of man-made objects in the image. Image segmentation into regions of uniform color or texture, and further analysis of these regions, yields opposite results for the natural and man-made categories. Important characteristics of the man-made images are primarily straight lines, straight boundaries, sharp edges, and geometry. On the other hand, regions in images of natural scenes have rigid boundaries and random distribution of edges.

Having thus identified a set of semantic categories that human observers reliably use to organize images, such as photographic images, in accordance with an aspect of these teachings a next step models these categories so that they can be used operationally in an image retrieval or browsing application. Unlike conventional approaches that use low-level visual primitives (such as color, color layout, texture and shape) to represent information about semantic meaning, the method focuses instead on the higher-level descriptors provided by the human observers. The descriptions that the observers provided for each category were examined with the following question in mind: Is it possible to find a set of low-level features and their organization capable of capturing semantics of the particular category?

As a starting point, the written descriptions of the categories gathered in the second experiment were used, and a list of verbal descriptors were devised that the observers found crucial in distinguishing the categories. These descriptors are then transformed into calculable image-processing features. For example, the verbal descriptor expressed as: (image containing primarily a human face, with little or no background scene), that is used to describe the category Portraits in the image-processing language can correspond to a descriptor expressed as: (dominant, large skin colored region). Or, the descriptor: (busy scene), used to describe the category Crowded Scenes with People in the image-processing language can correspond to a descriptor expressed simply as: (high spatial frequencies). The list may then be expanded by adding certain features considered useful, thereby producing a list of over 40 image-processing features referred to as the complete feature set (CFS).

As an illustration, a partial listing of the CFS is as follows: number of regions after image segmentation (large, medium, small, one region); image energy (high, medium, low frequencies); regularity (regular, irregular); existence of the central object (yes, no); edge distribution (regular/directional, regular/nondirectional, irregular/directional, etc.); color composition (bright, dark, saturated, pale, gray overtones, etc.); blobs of bright color (yes, no); spatial distribution of dominant colors (sparse, concentrated); presence of geometric structures (yes, no); number of edges (large, medium, small, no edges); corners (yes, no); straight lines (occasional, defining an object, no straight lines). Note that feature values in this representation are discrete, and the results of the corresponding image-processing operations are preferably quantized to reflect the human descriptions of the semantic content.

To determine which of these features correlate with the semantics of each category, and by way of example but not by limitation, a particular visualization tool was used (D. Rabenhorst, Opal: Users manual, IBM Research Internal Document.) Briefly, Opal visualization integrates numerous linked views of tabular data with automatic color brushing between the visualizations and an integrated math library. The basic concept is to offer multiple simultaneous complementary views of the data, and to support direct manipulation with the objects in these views. Interactive operations such as coloring data subsets, which are performed on any of the views, are immediately reflected in all the other active views. Using the Opal tool the experimental data was compared to the image-processing descriptors for a set of 100 images. Specifically, for each category an attempt was made to find a feature combination that discriminates that category against all the other images. For example, it was found that the feature combination and the following rule discriminates Cityscape images from other images in the set: Skin=no skin, Face=no face, Silhouette=no, Nature=no, Energy=high, Number of regions=large, Region size=small or medium, Central object=no, Details=yes, Number of edges=large.

A similar analysis was performed for all of the categories. It was discovered that within a certain category not all of the features are equally important. For example, all images in the Cityscapes category have high spatial frequencies, many details, dominant brown/gray overtones, and image segmentation yields a large number of small regions. These features are thus considered as Required Features for the Cityscapes category. On the other hand, most of the images from this category (but not all of them) have straight lines or regions with regular geometry, originating from the man-made objects in the scene. Or, although the dominant colors tend towards brown/gray/dark, many images have blobs of saturated colors, again because of man-made objects in the scene. Therefore, straight lines, geometry and blobs of saturated color are considered as Frequently Occurring Features for the Citycsapes category, but are not Required Features for the Cityscapes category.

Having thus determined the most important similarity categories, their relationships and features, an image similarity metric is then devised that embodies these perceptual findings and models the behavior of subjects in categorizing images. The metric is based on the following observations from the foregoing experiments: Having determined the set of semantic categories that people use in judging image similarity, each semantic category, $c_i$, is uniquely described by a set of features and, ideally, these features can be used to distinguish and separate the category from other categories in the set. Therefore, to describe the category $c_i$, it is preferred to use the following feature vector:

$$f(c_i) = [RF_1(c_i) RF_2(c_i) \ldots RF_{M_i}(c_i) FO_1(c_i) FO_2(c_i) \ldots FO_{N_i}(c_i)], \tag{4}$$

where: $\{RF_j(c_i) | j=1, \ldots, M_i\}$ is the set of $M_i$ required features, and $\{FO_j(c_i) | j=1, \ldots, N_i\}$ is the set of $N_i$ frequently occurring features for the category $c_i$.

To assign a semantic category to the input image x, what is needed is a complete feature set for that image, CFS(x). However, when comparing x to the semantic category $c_i$, it is preferred to use only a subset of features $f(x|c_i)$ that includes those features that capture the semantics of that category:

$$f(x|c_i) = [RF_1(x|c_i) RF_2(x|c_i) \ldots RF_{M_i}(x|c_i) FO_1(x|c_i) FO_2(x|c_i) \ldots FO_{N_i}(x|c_i)] \tag{5}$$

Then, the similarity between the image x and category $c_i$ is computed via the following metric:

$$sim(x, ci) = sim(f(x|ci), f(ci)) \tag{6}$$
$$= \frac{1}{N_i} \prod_{j=1}^{M_i} \tau(RF_j(x|ci), RF_j(ci)) \cdot \sum_{j=1}^{N_i} \tau(FO_j(x|ci), FO_j(ci))$$

where:

$$\tau(a, B) = \begin{cases} 1, & (\exists i) a = b_i \\ 0, & (\forall i) a \neq b_i \end{cases}, \text{ and } B = \{bi\}_{i=1,\ldots,I} \tag{7}$$

The similarity metric represents a mathematical description that reflects: To assign the semantic category $c_i$ to the image x, all the Required Features have to be present, and at least one of the Frequently Occurring features has to be present. Typically, the required feature $RF_1(c_i)$ has more than one value (i.e. I possible values), therefore the feature $RF_1(c_i)$ is compared to each possible value via Equation (7).

With regard now to image retrieval based on semantic categorization, and in addition to semantic categorization, the presently preferred metric can be used to measure similarity between two images, x and y as:

$$sim(x, y \mid ci) = \frac{1}{N_i} \prod_{j=1}^{M_i} \tau(RF_j(x \mid ci), RF_j(y \mid ci)) \cdot \sum_{j=1}^{N_i} \tau(FO_j(x \mid ci), FO_j(y \mid ci)), \quad (8)$$

$$sim(x, y) = \max {}_i(sim(x, y \mid ci)). \quad (9)$$

However, note that the similarity score is greater than zero only if both images belong to the same category. To allow comparison across all categories it is preferred to use a less strict metric. First introduce the similarity between images x and y, assuming that both of them belong to the category ci as:

$$sim(x, y \mid ci) = \frac{1}{2^{M_i + N_i}} \prod_{j=1}^{M_i} (1 + \tau(RF_j(x \mid ci), RF_j(y \mid ci))) \cdot \prod_{j=1}^{N_i} (1 + \tau(FO_j(x \mid ci), FO_j(y \mid ci))). \quad (10)$$

Assuming that $x \in ci$ and $y \in cj$, the overall similarity is defined as:

$$sim(x, y) = [sim(x, y \mid ci) + sim(x, y \mid cj)]/2. \quad (11)$$

In conventional practice in the area of image libraries the retrieval task is the task that is emphasized. Typically the user selects a query image, and the computer then operates to retrieve images that are similar to the query image. To do so, the implementation creates a vector of image features for the query image and computes the distance between that vector and the feature vectors created for all the images in the database. The vector typically contains features that are thought to contribute to human judgments of image similarity, e.g., color, texture and composition descriptors are typically included. All features are computed for every image, and the features are typically assigned equal weights.

The image retrieval method described above differs from the conventional approach in several ways. First, the feature vector is populated with perceptual features derived from experiments with human observers. These features capture the dimensions along which human observers judge image similarity. These are not general features, computed for each image, but are instead tuned to the semantic categories into which observers organize images. For example, the teachings of this invention do not require a color histogram for each image. Instead, the method uses those features that discriminate between semantic categories.

Second, in accordance with this invention the concept of perceptual categories is employed. To search the database 104, the method begins with the query image and computes the similarity measure between its feature vector and the feature vector for each of the perceptual categories. In the preferred metric not all features are weighted equally. Instead, the definition and use of "required" and "frequently occurring" features captures the notion that some descriptors are more important for some categories than for others. For example, color is critical for identifying an outdoor natural scene, but irrelevant for identifying a texture pattern. Long, straight boundaries between segments is a critical (required) feature for identifying "Outdoor architecture" but is irrelevant in identifying people. Instead, the critical feature for identifying people is the existence of a skin-colored image segment.

In the presently preferred embodiment a binary 0 or 1 weighting is implemented (e.g., the features are either included or not). If features are included, then the similarity between images within a category is proportional to the number of features they share in common (Hamming distance). However, it is within the scope of these teachings to employ a graded weighting of some or all of the features in order to better capture the notion that the required and frequently occurring features are not equally important. They may be more or less important overall, and more or less important within a particular category.

In one current image retrieval paradigm the criterion for success is whether the system 100 identifies all the existing identical or near identical images in the database 104. Although this can be of interest in some limited applications, such as cleansing a database of duplicate images, selecting the "best shot" of some person or object in a roll of film, or finding a picture of the Eiffel Tower with just the right sky color, in most real-world applications the user actually desires to find similar images. For example, a photojournalist may wish to begin an article with a wide-angle shot of a savannah with an animal. The photojournalist may have a photograph of a savannah, and wants the system 100 to aid in finding images that are similar, but that also include an animal. Or, a student may have a photograph of a walrus and may wish to identify other marine mammals. In this case the query image would be used as a seed for identifying similar images, and not a request for a near copy.

The ability to organize images in a database semantically gives the user control over the search process. Instead of being a black box which returns images computed by some unknowable criterion, the semantic library system provides a rich search environment.

The concept of organization by semantic category also provides a metaphor for examining the contents of an image library at a glance. At present there are tools for displaying all the files on an image CD. Unfortunately, these tools display the images as a matrix, according to their order on the CD. If the CD is arranged by category, the images are arranged by category, although these categories are not always useful. In accordance with these teachings the features of the images on the CD are computed, and the images may then be arrayed by category on the display screen 105B. If there are too many images to display at once, the image at the centroid of each category is preferably displayed, perhaps with an indication of the number of images organized within each category. A double-click on the canonical image using the input device 105A opens a page of images within that category, organized spatially according to image similarity. This technique is clearly superior to the prior art approach, as it provides the user with a sense of what images exist and how they are organized.

In addition to searching an image space for similar images, these teachings also provide a technique to browse and navigate through the image space. In the experiments discussed above candidate semantic categories were developed that human observers use to organize images, such as photographic images. By studying the confusions that people make in assigning images to categories, and by observing overlaps in the descriptive phrases they generate to describe and name categories, an insight was obtained into how the categories are organized. This is important for the design of a navigational system where the user can not only identify the category for an image, or retrieve images by similarity, but also use the semantic organization to navigate through image space. For example, a user exploring images in the "Green Landscapes" category may wish to locate a green landscape with human influence, or green landscapes with an animal. Since these are related categories, they may be organized spatially. The organization depicted in FIG. 9 may be employed as a map to guide the users' navigation, such as by using a joystick or a mouse to move around, i.e., navigate through, the space of images.

One mechanism for guiding the user to related categories can be provided by the system 100 where the similarity between the query image and the other images in a category are computed not by a Hamming distance, but by a more sophisticated scheme where different weights are applied to different features in the category. In this scheme, the ordering of the matching images within a category defines a trajectory for leading the user through the image space. For example, an image of the Eiffel Tower may take the user to the "Outdoor Architecture" category. If the query image is taken from beneath the structure, it would match more strongly those images in the "Outdoor Architecture" category that also had darker luminance and warmer colors. Following that trajectory along the distance gradient, the user may be led towards the "Objects Indoors" category.

A further extension of the teachings is to integrate the above-described methods with work on textual semantic networks. For example, if the user were searching for a web site with a picture of the Eiffel Tower, the web agent may include a text engine to identify the key words, but also an image agent that reports which sites also included a photograph of "Outdoor Architecture".

The system 100 enables the user to input an image, and the system 100 then operates to identify a category for that image and to output an ordered set of similar images. Further in accordance with these teachings the user interacts with the system 100 to refine the search by interactively identifying subsets of images, and using these as subsequent queries. For example, the user may begin with a ski scene, which is identified as "Winter and Snow". The system 100, in one instantiation, has no way of knowing whether the user is looking for images of the tundra wilderness or for images of ski clothing. In order to provide more information to the system 100 the user may interacts with the GUI 105 to outline a "region of interest," either in the query image or in one of the retrieved images. The system 100 then computes the feature vectors for that subset of the image, and then uses the subset of feature vectors as a subsequent query. The subset of feature vectors may simply provide an improved set of weights for the desired features, or it may even propel the user into a new category. By having the capability of identifying the region of an image that best matches the current interest, the user can dynamically control the navigation process.

These teachings may also be employed where the database 108 is located remotely and is reachable through the data communications network 102. In this case characterizing the relationship of the selected image to another image in the database 108 by applying the perceptually-based similarity metric can be accomplished in conjunction with a text-based search algorithm to retrieve a multi-media object containing text and image data from the remote location. In this case a method includes identifying a query image; determining a CFS of the query image; and using the determined CFS to compare the query image to the images stored in the remote database 108, where the database 108 is accessed via the server 109 that is coupled to the internet 107, and where the query image forms a part of a query that also includes a textual component.

Turning now more particularly to the teachings of this invention, it has been shown that for images that represent a semantically well-defined set, combinations of the low level global and local features, such as color composition, lines, region color, boundaries, shape and texture, frequency information, blob information, etc., can be used to capture image semantics. Given such a set, and given a balanced set of image features, the semantic image categorization problem can be defined through the following two steps. 1) for each semantic category $c_i$, determine a feature vector $f(c_i)$ that discriminates that category from other images, and 2) given the feature vectors for all the categories, categorize image x by finding:

$$\min_i \{dist(f(x|c_i), f(c_i))\} \quad (12)$$

where: $(x|c_i)$ is a feature set for image x, assuming that it belongs to the category $c_i$, and $dist(\cdot)$ is some distance metric between the feature vectors $f(x|c_i)$ and $f(c_i)$.

This approach is now expanded and applied to automatic categorization, browsing and retrieval in databases, described herein in the exemplary context of medical images. The use of these teachings in the context of medical images is not, however, to be construed in a limiting sense upon the practice of this invention.

The presently preferred embodiment is based at least in part on the hypothesis that different types of imaging modalities, as well as different classes of medical images within the same modality, represent semantically well-defined sets. Given a medical database comprising different imaging modalities (for example, X-ray, MRI, ultrasound, microscopy, photography, medical diagrams, etc.) the goal is to: 1) provide versatile global and regional image features as a basis for the semantic descriptors, 2) develop feature combinations that capture the visual characteristics of each modality, 3) implement an image categorization metric that enables intelligent browsing and navigation of the image repository. Since images within the same modality represent a semantically well-defined set, image classification and retrieval share the same goal. Therefore, the classification method can be further used as a similarity metric for searching for similar images.

Figure 10:
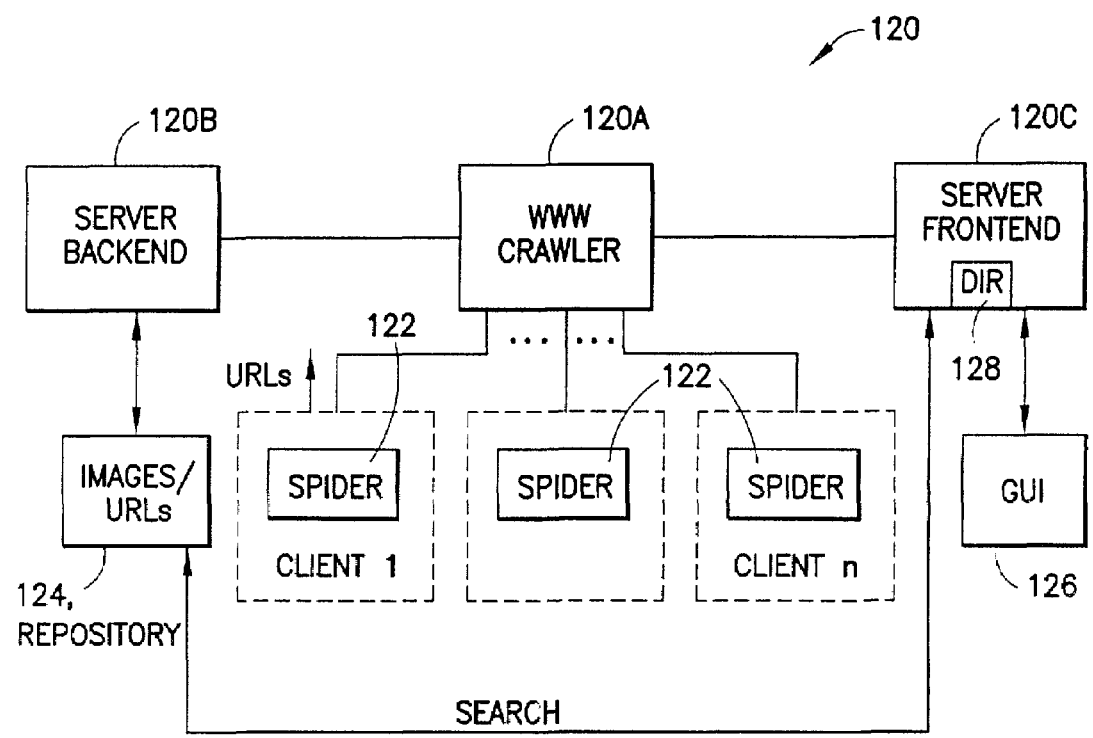
FIG. 10 is a high level view of an Internet portal that provides access to the database.

FIG. 10 shows a high level view of an Internet portal 120 that provides access to the database 108. The Internet portal 120 can be implemented on the server 109 of FIG. 1, and may be used for browsing online medical databases. The Internet portal 120 includes three logical parts that operate independently as follows.

Logical part 120A implements a distributed World Wide Web (web) crawler. Numerous "tiny spiders" 122, starting independently from arbitrary home nodes, traverse the web no further than a certain predefined distance. The metric used by the spiders 122 to measure how far they are from their home node reflects their preference for staying within the same physical server, which limits the depth of the search. Thus, each spider 122 may work within a domain around its home node and completes its traversal in minutes on the average WWW client (e.g., any personal computer). The spiders 122 send the URLs of the found images back to the common server 109. The server 109 receives all the packets and eliminates redundancies. As will be described in further detail below, the spiders 122 execute on the computer hardware of users, and report the URLs of located images back to the logical part 120A.

Logical part 120B is the server back-end. This part computes the image features. The image features, along with their URLs and the URLs of a document referencing them, are stored in a repository 124.

Logical part 120C is the server front-end. The front-end of the search engine runs on the HTTP server and searches the repository according to the queries of the users.

Users interact with the Internet portal 120 through a graphical user interface (GUI) 126, typical for Internet search engines. All actions supported by the Internet portal 120 are based on the categorization of images into classes representing different imaging modalities, and their subclasses. Each imaging modality is modeled with a different combination of features. The feature selection and extraction process is further described below. Images are assigned to classes using the categorization method that is also described below. Additional image classes and subclasses can be added at any time. The queries can be formulated in two ways. The first way by the use of functions, such as X-rays( ) or Tissues( ) for the example of a medical database. All of the available functions are listed on a front page of the Internet portal 120 web directory 128. The functions implement the automatic image categorization algorithm, to retrieve all the images from one of the predefined image classes. Another level of interaction can be achieved by combining these functions with lower level features using Boolean comparison and arithmetic operators. In that the features are related to the human perception of semantic content, it is possible to use "natural language" to query a database. The web can be also searched using combinations of functions, features and text keywords.

A discussion is now made of the presently preferred feature selection and extraction algorithms for use in the semantic categorization of medical images. It is again noted that while this invention is described in the context of a medical database, these teachings are not limited for use with only medical images.

By way of introduction, even an untrained subject can distinguish between certain imaging modalities, since they have an entirely different visual appearance. For example, one can readily make a distinction between an X-ray and a tissue photograph, due at least to their very different color properties. At a more sophisticated level, one may also distinguish between ultrasound, X-ray and MRI images, due to the substantial difference in their grayscale contrast. Therefore, at a first level of semantics global features are employed to support this level of knowledge. However, medical knowledge further arises from anatomical and physiological information. Therefore, at the second level of semantics, regional features are used to support semantic queries. For example, regional features are used to distinguish between different organs and body parts. On a deeper level, these features may be used for diagnostic queries, such as examining an X-ray image for the presence of a tumor.

An important goal is thus to design a feature set that is linked to human perception of image content. Such a set allows for the presence of an efficient categorization metric, as well as intuitive queries. Consequently, the features in the set are linked to some of the semantic attributes used to describe image appearance. Some examples of these attributes are "background is black", or "there is one round object in the center", or "image is monochromatic", or "there is a human in the picture", etc. For each image there is therefore extracted a set of semantically elevant global and local features through the following processing steps.

Figure 11:
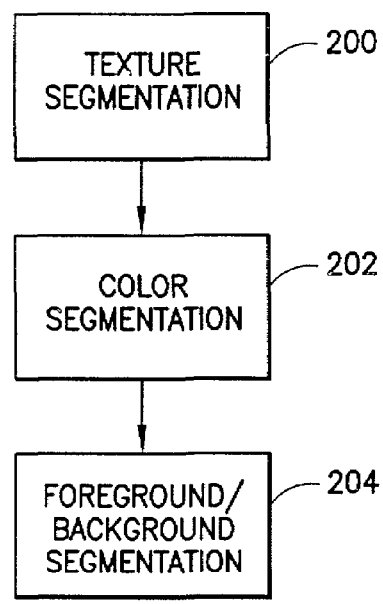
FIG. 11 is a logic flow diagram that illustrates three segmentation processing steps for an input image.

Referring to FIG. 11, the input image is first subjected to the following three types of segmentation. The first segmentation at Step 200 is texture segmentation, followed by color segmentation at Step 202, and then foreground/background segmentation at Step 204. Texture segmentation 200 has two goals. The first goal is to determine if the image is uniform in the texture domain (in which case it most likely represents a tissue). The second goal of texture segmentation is to provide a texture map, which is to subsequently used to provide additional information about specific image regions. The original image is then subjected to the color segmentation 202. Each relevant region from the color segmentation is assigned the structure containing the information about its size, boundary, texture (from the texture map), mean color and a colorname (for example red, light pink, black, dark gray, etc.). In the third step, the texture and color maps are combined to achieve the foreground/background segmentation 204, i.e. to determine if there is a dominant object (or objects) in the image. For each relevant object the algorithm preferably computes simple shape features (boundary, eccentricity, moments, symmetry features etc.), as well as color and texture properties.

In the presently preferred embodiment, a texture map is generated by computing a set of directional edge maps, followed by a region growing procedure. For color segmentation it is preferred to use a mean-shift algorithm, such as one described by D. Comaniciu, and P. Meer, "Mean Shift Analysis and Applications", *Proc. IEEE Int. Conf. Computer Vision,* ICCV'99, pp. 1197–1203, Kerkyra, Greece, 1999. For each extracted region, a presently preferred color naming procedure is carried out by comparing the average region color with a set of standard colors described in the *ICCS NBS Color dictionary,* see K. L. Kelly, and D. B. Judd, "The ISCC-NBS color names dictionary and the universal color language", *NBS Circular* 553, Nov. 1, 1955, using the $L^2$ norm in the Lab color space.

Another important semantic feature is the presence of humans in the image, i.e., the presence of skin. A presently preferred algorithm for the detection of skin regions is based on a geometric method where image pixels are interpreted as points in a four dimensional (4D) Euclidian space. The coordinates of a pixel in this space are the Lab color coordinates and the measure of the color variation. The latter is totally encoded in the spatial Jacobian of (L,a,b), but only its Euclidean norm n is actually used. To build a skin color model in this space, "skin pixels" collected from a training set of 260 images are used. A manifold of the skin color is then reconstructed via 4D anisotropic diffusion. This diffusion is achieved through the resolution of a dedicated Partial Differential Equation. The skin regions are identified by computing the distance between each relevant region and the skin manifold.

All of the regional features are then combined to provide global descriptors. These include the number of regions, number of blobs, number of regions with specific color and measures of local and global contrast. Furthermore, the color names from all relevant regions are combined into a color name histogram to determine a color appearance of the image. The color name histogram generates descriptions such as grayscale, monochromatic, flesh, pink overtones and graphic colors. In many cases these descriptions only are capable of capturing image semantics. For example, due to bright colors, medical diagrams are often characterized with "graphic colors". Similarly, certain stainings in histology create "monochromatic appearance" with "pink or purple overtones", while photographs of the internal tissues have color composition described as "flesh".

Figure 15A:
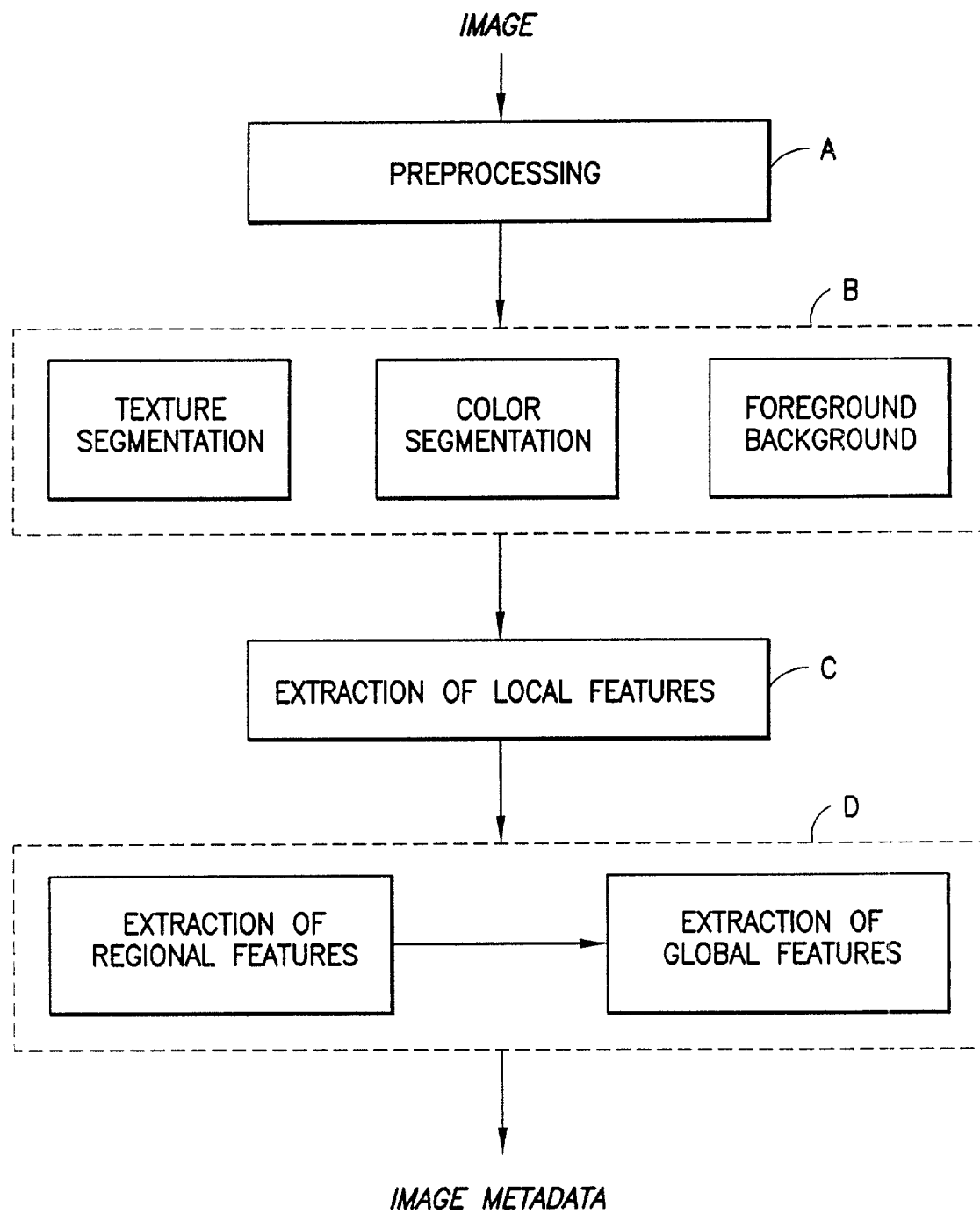
FIG. 15A is a logic flow diagram showing a feature extraction process.
Figure 15B:
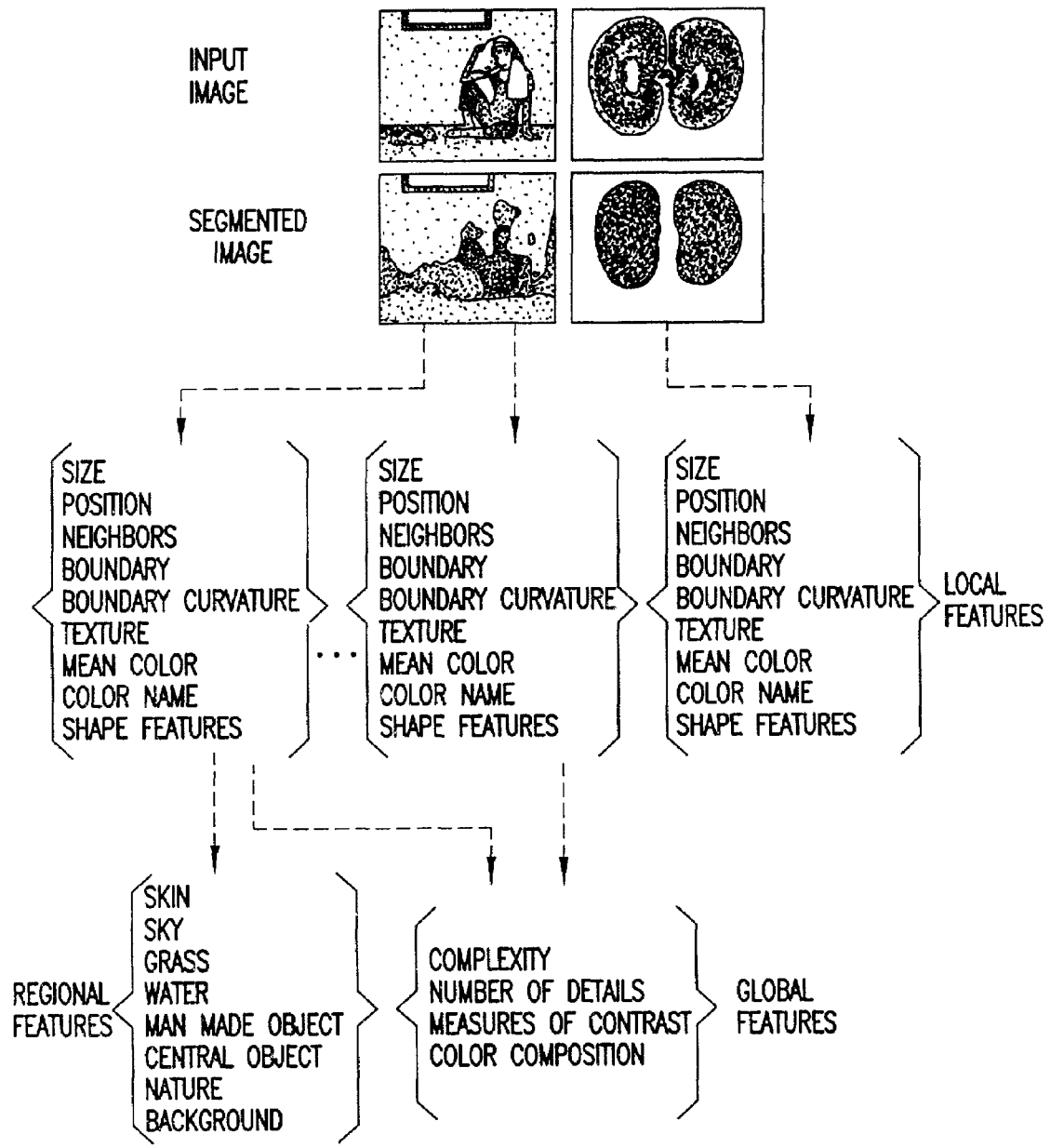
FIG. 15B illustrates two exemplary input images that are acted on by the feature extraction process of FIG. 15A.

Referring to FIGS. 15A and 15B there is provided an overview of the feature extraction process. The logic flow diagram of FIG. 15A may also be viewed as a block diagram of a feature extraction processor. At Step A of FIG. 15A an input image (two examples of which are shown in FIG. 15B) is provided to a preprocessor that performs any suitable image processing tasks, such as the elimination of noise and image artifacts, image scaling, rotation and so forth. The end result is a preprocessed image that is input to a segmentation block at Step B. The segmentation block operates in parallel or in series on the image to perform texture segmentation, color segmentation and foreground/background segmentation, as described above. In general, color segmentation partitions the image into regions of consistent color. While these regions typically do not constitute meaningful objects, they can be important descriptors of certain semantic properties. On the other hand, foreground-background segmentation detects important objects. The regions resulting from color segmentation can be referred to as relevant regions, while the objects detected through foreground-background segmentation can be referred to as relevant objects. FIG. 15B shows two examples of segmented images corresponding to the two input images. At Step C the segmented image is applied to a local features extraction block where local image features are identified and extracted. Presently preferred, but not limiting, local features include: size, position, neighbors, boundary, boundary curvature, texture, mean color and shape features. Note in FIG. 15B that a set of local features can be extracted from each different segment of the segmented image. The extracted local features are then acted on in Step D to extract regional features, followed by an extraction of global image features. As is shown in FIG. 15B, regional features can include, but are not limited to: skin, sky, grass, water, flowers, snow, texture, man made objects, a central object, nature and background. The global features can include, but are not limited to: complexity, number of details, measures of contrast, histogram of color names, color composition, number of objects, number of regions, number of straight lines, number of regular curves, number of blobs, energy (i.e., concentration of edges in a certain region), spatial activity (i.e., number of objects in a certain region) and symmetry (or lack thereof). The end result is a set of image metadata that is suitable for use in searching for and identifying stored images, such as during an image search or query procedure that is performed over a data communications network.

A description is now made of image categorization. The initial image categories are preferably established according to the most common medical imaging modalities. These include, but need not be limited to, X-rays (with different subclasses according to the body parts), MRI, histological stainings (again divided according to the different types of stainings), micrographs, photographs of internal organs and photographs of internal tissues. For each semantic category there is determined a feature combination that best captures the semantics of that category. The feature selection can be conducted on, for example, a training set of 200 images. In modeling the semantics of each category, the previous perceptual findings can be followed. Namely, within a certain category, not all the features are equally important. For example, all histological images obtained with the same staining process have the same color composition. This feature is thus considered as a required feature for the particular class. On the other hand, most of the images from this category (but not necessarily all of them) have uniform texture properties, or a large number of small/medium irregularly distributed blobs. Therefore, texture properties, blob number and blob size are considered as frequently occurring features for this category.

According to the presently preferred model, each semantic category $c_i$ is "uniquely" described by the set of features $S^c_i$. Ideally, these features can be used to separate $c_i$ from other categories in the set. To test if the input image x belongs to the category $c_i$ it is preferred to use only the features that are important for this category. This is done according to the following technique. The semantics of each category $c_i$ are captured by the following four sets:

1), 2) The set of features, $S^c_i$, that are representative for the category, and their values, $V^c_i$ $$S^{c_i} = \{\{RF_j^{c_i}\}_{j=1,\ldots,M_i}, \{FO_k^{c_i}\}_{k=1,\ldots,N_i}\} \qquad (13)$$

$$V^{c_i} = \{V_j^{c_i}\}_{j=1,\ldots,M_i+N_i} \qquad (14)$$

where: RF and FO are the required and frequently occurring features for the category $c_i$. For the image x, the values involved in testing if $_{x \in c_i}$ are then $$S^{c_i}(x) = \{S_j^{c_i}(x)\}_{j=1,\ldots,M_i+N_i} = \{\{RF_j^{c_i}(x)\}_{j=1,\ldots,M_i}, \{FO_k^{c_i}(x)\}_{k=1,\ldots,N_i}\} \qquad (15)$$

3) The set of operators, or functions, $O^{c_i}$, describing how $S^{c_i}(x)$ will be compared to $V^{c_i}$.

$$O_{c_i} = \{O_j^{c_i}(S^{c_i}(x)_j^{c_i}, V_j^{c_i}, P_j^{c_i}) | O_j^{c_i} \in [0,1]\}_{j=1,\ldots,M_i+N_i} \qquad (16)$$

where:

$$P_{c_i} = \{P_j^{c_i}\}_{j=1,\ldots,M_i+N_i} \qquad (17)$$

is the set of parameters involved in the comparison.

The comparison is then performed according to the following metric:

$$sim(x, ci) = \frac{1}{N_i} \left[ \prod_{j=1}^{M_i} O_j^{c_i}(RF_j^{c_i}(x), V_j^{c_i}, P_j^{c_i}) \right] \cdot \left[ \sum_{j=M_i+1}^{N_i+M_i} O_j^{c_i}(FO_{j-M_i}^{c_i}(x), V_j^{c_i}, P_j^{c_i}) \right]$$

$$sim(x, c_i) > 0 \Rightarrow x \in c_i$$

Note that, according to the foregoing metric, to classify image into a semantic category, all of the required and at least one of the frequently occurring features for that category have to be present.

Figure 12:
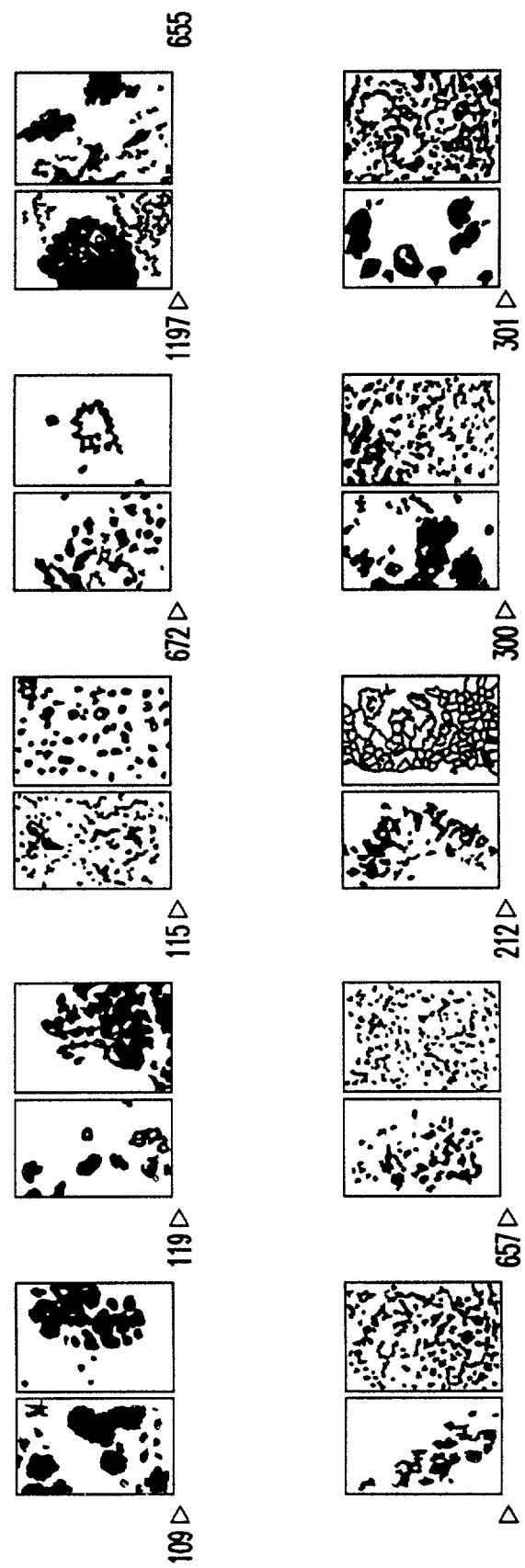
FIG. 12 is an example image categorization results for images belonging to a category, "Stainings:Staining Type-Papanicolau"
Figure 13:
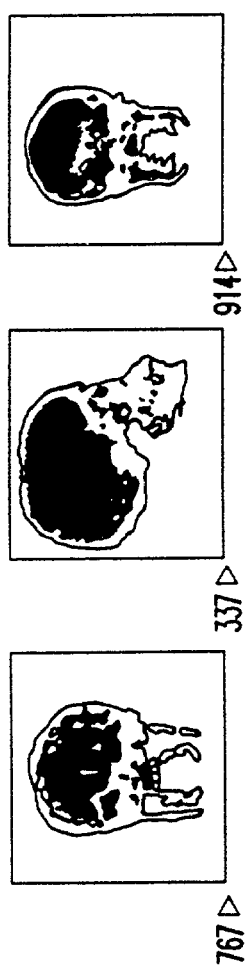
FIG. 13 shows the results of a query generated to find an image of a skull.

FIG. 12 shows images displayed on a typical screen from the Internet portal, with images classified into "Stainings/Papanicolau" category. The query was performed on a 2000 images "crawled" from the medical databases registered on the WWW. In addition to providing semantic categorization into preselected imaging modalities, the Internet portal allows users to compose their own queries, by typing in a query window. Since the feature set is semantically based, the users can write queries in the same way they would describe images. For example, to find X-ray images of a human skull, the user may compose the following query:

> texture = no AND composition = grayscale AND
> 500 < contrast < 6000 AND
> number of relevant objects = 1 AND
> eccentricity < $T_{round}$ AND y – symmetry > $T_{symy}$ AND
> $T_{omin}$ < object size < $T_{omax}$ AND background = black where $T_{cmin}$, $T_{cmax}$, $T_{round}$, $T_{symy}$, $T_{omin}$ and $T_{omax}$ are thresholds for contrast, eccentricity, y-symmetry, and object size. In this particular example, these values are 2.6, 0.7, 20, and 50. The results of this query are shown in FIG. 13.

Figure 14:
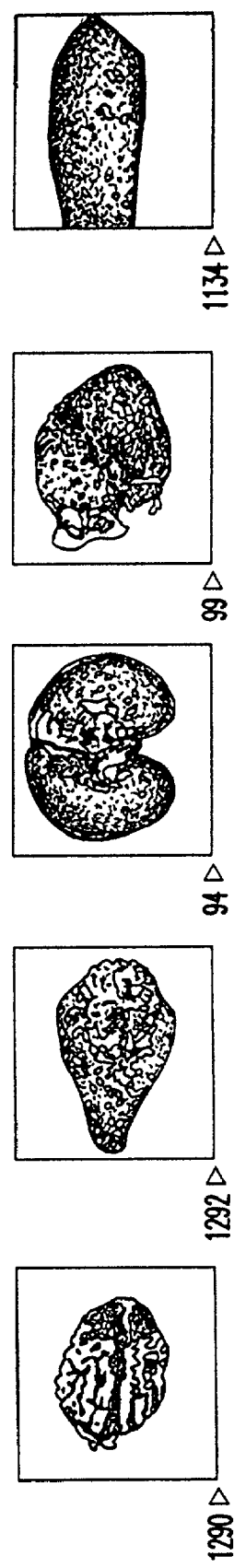
FIG. 14 shows an example of image retrieval, where the image 1290 is the query image, followed by four closest image matches, where all of the images belong to the category "Organs"

Since medical images represent a semantically well-defined set, image categorization and retrieval share the same goal, and the foregoing metric can be used to retrieve similar images from the database. In this case, the feature set for the query image will be taken instead of the feature set for the image class. Note an important property of this metric for the application in medical imaging—the similarity score is greater than zero only if both images belong to the same category. An example of the image retrieval results is shown in FIG. 14.

Described above has been a method for semantic description, classification and retrieval of images, presented in the context of medical images, such as medical images gathered on the WWW. The results demonstrate that accurate categorization can be achieved by observing the important visual properties of each imaging modality, and developing the features that model these properties along perceptual dimensions. Since the method provides basic semantic knowledge about the image it may be used as an interface to the domain specific content-based medical image retrieval and analysis algorithms.

The medical image related aspects of this invention may also employ the text-based search algorithm executed by the server 109 to retrieve a multi-media object from the remote database 108 and/or by the data processor 101 to retrieve a multi-media object from the database 104.

The foregoing aspects of this invention is of particular importance, as the use of databases and the Internet is growing rapidly, driving the need to develop better search and navigation tools. While at present keywords and text-based queries are the predominant approach in database management, the use of keywords and low-level image descriptors does not capture the meaning of an image. As a result, it is becoming increasingly important to provide visual searching and browsing capabilities. Potential applications include, but are not limited to, online catalogs, Internet search engines, news and media, biomedical databases and digital museums. The ability to provide, in accordance with this aspect of the invention, good semantic descriptors that are derived from images contained in a document or some other image source facilitates the development of an improved browser. The improved browser, which could be referred to as a "visual browser", enables users to access documents through the visual content of the documents.

An aspect of this invention is thus the development of efficient and meaningful image features, and indexing, annotation and content summarization schemes, and using these for performing intelligent search, retrieval and browsing of the web documents and other image sources.

As has been described above, it is important to derive an understanding of, so as to be able to model, the important semantic categories that drive visual perception. Subjective experiments were performed for: a) developing and refining a set of candidate perceptual categories in the domain of photographic images (such as portraits, people, landscapes, objects, interiors, architecture, animals, etc.), and b) discovering a combination of low-level descriptors that best describe each category. Based on the findings from these experiments the feature extraction algorithms were developed to facilitate indexing and annotating images, and for searching the database using the semantic concepts.

Also, in order to index images on the Internet, the image web robot is employed, the robot employing the spiders 122 shown in FIG. 10 and described above. The spiders 122 start independently from arbitrary home nodes and crawl the web no further than some certain predefined distance, such as some predetermined number of "clicks" from the starting point. The spider 122, when locating a file or other organization of data, referred to generally herein as a document, that contains an image (such as would be indicated from the file extension: e.g., tif, jpeg, etc.), sends the URL of the found image back to the common web crawler server 120. The URLs of documents that are referenced by the image and/or that reference the image are also preferably also retrieved and returned. The server back-end 120B then accesses and retrieves the image using the returned URL, computes the image features (image metadata, as described above with respect to FIGS. 15A and 15B) and stores the image metadata in the repository 124 along with associated image URLs and preferably the URLs of image-related and referenced documents.

In some respects one of the spiders 122 can resemble a more conventional Internet searching tool, i.e., a web crawler implemented using a distributed program running in several interconnected computers, following links on the web and gathering information about the traversed documents.

However, in conventional systems, the web crawler runs in one or more large machines on the server side. These machines maybe owned by a company or organization that provides the search engine. In contradistinction, in this invention each spider 122 runs on the client's side, i.e., on the client's computer hardware.

A user of the searching system (a person who launches a web page of the searching system of this invention with the intention of searching for images) also launches an applet embedded in the search engine portal. The rationale is that spider 122 uses a minimal amount of computational resources, and that the user is not disturbed by the operation of the spider 122, and does not perceive that the spider 122 is concurrently executing in the background. A significant advantage of this approach is the potentially large number of users, and hence the potentially large number of spiders 122 that can exist. As the system grows in size by the number of users, then the number of spiders 122 grows as well, as does the size of the database 104. Initially, if there are no users, a number of spiders 122 can be launched artificially to build an initial database 104.

Each individual spider 122 need not aware of other spiders run by other clients. It is only aware of a starting point on the web from which it crawls the web searching for images and sends their URLs back the server 120. The search starting point (the seed) can be defined by the user if, for example, the user wants to include the images of his own web site in the database. By default, the seed can be picked randomly by each spider 122, or it can be communicated from the server at the request of a spider 122.

As the spiders 122 work independently of one another it is possible that two spiders will send the same image URL back to the server 120, which checks for this condition and eliminates redundancies.

As for firewalls, the user launches the spider 122 as soon as the has access to the system portal. While a security concern is that, by default, a java applet cannot access other computers on the web, except that from which it has been downloaded. But this is a default behavior, and the user can explicitly grant this permission to the applet.

This aspect of the invention also provides an Internet searching tool that allow users to search the Internet using not only text, but also image-driven data, to present the search results in both text and image forms, and also to browse the Internet based on visual attributes of one or more images of interest.

For example, assume that a user is interested in learning more about Paris and its tourist attractions. Typing "Paris monuments" as a query in any commercial web search engine will typically provide hundreds of results. An alternative technique made possible by this invention is to use a visual browser window, where images from these web pages are organized "semantically" according to meaningful categories. This provides the user with another, entirely different view of the data, and the user can employ both textual and image views for further exploration.

It is also within the scope of these teachings for the user to input an image, such as an image of the Eiffel Tower, and to use this image as a search query for locating similar images and, more desirably, semantically similar images that, in this case, would be images of other monuments and attractions found in Paris. The input image is subjected to the process shown in FIG. 15A, and the resulting image metadata are used as search criteria for locating other images having similar metadata that were located and returned by the web-crawling spiders 122. A text-based search could also be used in conjunction with the image-based search.

This aspect of the invention thus provides an Internet searching tool that includes an Internet searching robot with at least one autonomous searcher, the spiders 122, that locate images and return image location data (URLs). A processor (120) is responsive to returned image location data for accessing a located image for segmenting the located image and for extracting features from the located image for obtaining a set of image metadata, as shown in FIGS. 15A and 15B. Storage is provided, such as the repository 124, for storing the set of image metadata, as is a user interface (GUI) 126 for entering queries from client users for searching the storage and for returning images having image metadata that is relevant to a user query. The user query can be a text-based query, an image-based query, or a combination of text/image-based query. The processor is responsive to the image-based query for segmenting an input image and for extracting features from the input image for obtaining a set of input image metadata, and for using the input image metadata when searching the storage.

It should be noted that while the foregoing methods and system can be used to find similar images, they can also be used to locate similar "topics", such as documents that contain similar visual information. Thus, while the teachings of this invention can be used to advantage for searching databases, the teachings of this invention can be used as well for the more general case of searching databases having entries that contain image data and other data, such as textual data.

Thus, while methods and a system have been disclosed for the semantic organization and retrieval of digitally stored images based on low-level image descriptors derived from perceptual experiments, it should be appreciated that these teachings are not to be limited to only the presently preferred embodiments disclosed herein, nor is this invention to be limited in any way by the specific examples of image categories and subject matter that were disclosed above. For example, these teachings can be used to discover the semantic meaning of images stored in both image and video databases, video collections, image and video streams, or any form of image data. As but one example, an input or query image can be one obtained from real-time or substantially real-time streaming video that is input to the system 100 via, for example, one of the peripheral devices 110. By periodically so obtaining a query image, the input streaming video can be classified according to semantic content, as but one example.

Thus, it should be apparent that these teachings are clearly not intended to be limited only to processing a collection of photographic images stored in a computer memory device, or on some type of computer readable media. As such, the various descriptions found above should be viewed as being exemplary of the teachings of this invention, as these descriptions were provided as an aid in understanding the teachings of this invention, and were not intended to be read in a limiting sense upon the scope and practice of this invention.

What is claimed is:

1. A computer implemented method for characterizing images and determining image similarity based on semantic meaning of images, comprising:

deriving a plurality of semantic categories for representing important semantic cues in images, where each semantic category is modeled through a combination of perceptual features that define the semantics of that category and that discriminate that category from other categories;

for each semantic category, forming a set of the perceptual features comprising required features and frequently occurring features;

comparing an image to said semantic categories; and classifying said image as belonging to one of said semantic categories if all of the required features and at least one of the frequently occurring features for that semantic category are present in said image.

2. A method as in claim 1, where a database stores image information, where the image information comprises at least one of already classified images, network locations of already classified images and documents containing already classified images, and where said database is searched for images matching an input query.

3. A method as in claim 2, where said input query comprises an input image, further comprising extracting features from said input image and applying a metric to determine the semantic category for said input image.

4. A method as in claim 2, where said input query comprises an input image, further comprising processing said input image and comparing said input image to each semantic category using a metric that computes a similarity measure between the features used to describe the semantic category and corresponding features extracted from said input image; and assigning said input image to the semantic category that corresponds to a highest value of the similarity measure.

5. A method as in claim 2, where said image information is obtained at least in part through the Internet.

6. A method as in claim 1, where said images are medical images.

7. A method as in claim 5, where said images are medical images.

8. A method as in claim 2, further comprising searching said database for at least one image or image-related document that satisfies at least one threshold established by said search query.

9. A method as in claim 2, where the database is located at a remote location and is searched by issuing a query to a database server through a data communications network.

10. A method as in claim 9, and further comprising retrieving an image or image-related document from the remote database.

11. A method as in claim 2, where the database is located at a remote location and is searched by issuing a query to a database server, through a data communications network, in conjunction with a text-based search algorithm executed by said server to retrieve a multi-media object from the database.

12. A method as in claim 2, where the database comprises image information obtained from a plurality of autonomous searchers that execute in client computers and that return URLs corresponding to located image data and image-related documents.

13. A method as in claim 1, further comprising segmenting an image by employing texture segmentation, color segmentation and foreground/background segmentation.

14. A method as in claim 13, where texture segmentation includes forming a texture map.

15. A method as in claim 14, where color segmentation includes forming a region map.

16. A method as in claim 15, where foreground/background segmentation includes using the texture map and the region map to determine if there is at least one dominant object in the image, and forming an object map.

17. A method as in claim 16, where the image, texture map, region map and object map are further processed to compute, for each region in the region map and for each object in the object map, a set of local features comprising information descriptive of size, boundary, neighbors, boundary curvature, texture, mean color, color name, and shape properties for that region/object.

18. A method as in claim 13, where local features are analyzed to compute regional features for indicating a presence of semantic cues.

19. A method as in claim 18, where said semantic cues comprise at least one of skin, sky, grass, snow, nature, water, man-made objects, man-made blobs, flowers and texture.

20. A method as in claim 13, where local features are combined to compute global features that describe a global appearance of the image.

21. A method as in claim 20, where said global features comprise at least one of number of details, histogram of color names, description of color composition, number of regions, number of blobs, number of objects, number of straight lines, number of regular curves, energy, spatial activity, symmetry and measures of contrast.

22. A data processing system comprising a data processor, a graphical user interface and a memory that stores a database containing image information, where the image information comprises at least one of already classified images, network locations of already classified images and documents containing already classified images, said data processor operating in accordance with a stored program for classifying images by deriving a plurality of semantic categories for representing important semantic cues in images, where each semantic category is modeled through a combination of perceptual features that define the semantics of that category and that discriminate that category from other categories; said data processor, for each semantic category, forming a set of the perceptual features comprising required features and frequently occurring features; comparing an image to said semantic categories; and classifying said image as belonging to one of said semantic categories if all of the required features and at least one of the frequently occurring features for that semantic category are present in said image, said data processor storing image-related classification data in said database.

23. A data processing system as in claim 22, where said database is searched for images matching an input query.

24. A data processing system as in claim 23, where said input query comprises an input image, and where data processor extracts features from said input image and applies a metric to determine the semantic category for said input image.

25. A data processing system as in claim 23, where said input query comprises an input image, and where said data processor processes said input image and compares said input image to each semantic category using a metric that computes a similarity measure between the features used to describe the semantic category and corresponding features extracted from said input image; and assigns said input image to the semantic category that corresponds to a highest value of the similarity measure.

26. A data processing system as in claim 22, where said image information is obtained at least in part through the Internet.

27. A data processing system as in claim 22, where said image information is comprised of medical image information.

28. A data processing system as in claim 22, where said image information comprises data obtained from a plurality of autonomous searchers that execute in client computers and that return URLs corresponding to located images.

29. A data processing system as in claim 23, where said data processor searches said database for locating at least one image that satisfies thresholds established by said search query.

30. A data processing system as in claim 23, where the database is located at a remote location and is searched by issuing a query to a database server through a data communications network.

31. A data processing system as in claim 30, and further comprising retrieving an image through said data communications network.

32. A data processing system as in claim 23, where said database is located at a remote location and is searched by issuing a query to a database server, through a data communications network, in conjunction with a text-based search algorithm executed by said server to retrieve a multi-media object.

33. A data processing system as in claim 23, where said image information comprises medical image information and is searched by issuing a query to a database server through the Internet.

34. A data processing system as in claim 23, where said data processor segments an input image by employing texture segmentation, color segmentation and foreground/background segmentation.

35. A data processing system as in claim 34, where texture segmentation includes forming a texture map.

36. A data processing system as in claim 35, where color segmentation includes forming a region map.

37. A data processing system as in claim 36, where foreground/background segmentation includes using the texture map and the region map to determine if there is at least one dominant object in the image, and to form an object map.

38. A data processing system as in claim 37, where the input image, texture map, region map and object map are further processed to compute for each region in the region map and for each object in the object map, a set of local features comprising information concerning size, boundary, neighbors, boundary curvature, texture, mean color, color name, and shape properties for that region/object.

39. A data processing system as in claim 34, where local features are analyzed to compute regional features, indicating a presence of semantic cues.

40. A data processing system as in claim 39, where said semantic cues comprise at least one of skin, sky, grass, snow, nature, water, man-made objects, man-made blobs, flowers and texture.

41. A data processing system as in claim 39, where local features are combined to compute global features that describe a global appearance of the image.

42. A data processing system as in claim 41, where said global features comprise at least one of number of details, histogram of color names, description of color composition, number of regions, number of blobs, number of objects, number of straight lines, number of regular curves, energy, spatial activity, symmetry and measures of contrast.

43. A computer program embodied on a computer readable media for directing a computer to execute a method for processing digitally represented images, comprising program instructions for classifying images by deriving a plurality of semantic categories for representing important semantic cues in images, where each semantic category is modeled through a combination of perceptual features that define the semantics of that category and that discriminate that category from other categories, where for each semantic category said program instructions form a set of the perceptual features comprising required features and frequently occurring features, compares an image to said semantic categories and classifies said image as belonging to one of said semantic categories if all of the required features and at least one of the frequently occurring features for that semantic category are present in said image.

44. A computer program as in claim 43, where classified images are stored in a database, and where classified images or network locations of classified images are added to said database after being assigned to one of said semantic categories.

45. A computer program as in claim 43, were said images are obtained at least in part through the Internet.

46. A computer program as in claim 44, further comprising searching said database for at least one image or image-containing document that satisfies thresholds established by a search query.

47. A method as in claim 1, where said perceptual features and their combinations are derived through subjective experiments performed with human observers.

48. A system as in claim 22, where said perceptual features and their combinations are derived through subjective experiments performed with human observers.

49. A computer implemented method for characterizing images and determining image similarity based on semantic meaning of images, comprising:
for each semantic category of a plurality of semantic categories, forming a set of perceptual features comprising required features and frequently occurring features, where each semantic category is modeled through a combination of perceptual features that define the semantics of that category and that discriminate that category from other categories;
determining features of an image;
comparing features of the image to the sets of perceptual features of the semantic categories; and
classifying the image as belonging to one of the semantic categories if all of the required features and at least one of the frequently occurring features for that semantic category are present in the features of the image.

50. A method as in claim 49, where the perceptual features and their combinations are derived through subjective experiments performed with human observers.

51. A method as in claim 49, where comparing further comprises computing a similarity measure between the features used to describe the semantic category and corresponding features determined from the image; and where classifying further comprises assigning the image to that semantic category that corresponds to a highest value of the similarity measure.

52. An apparatus comprising:
means for forming, for each semantic category of a plurality of semantic categories, a set of perceptual features comprising required features and frequently occurring features, where each semantic category is modeled through a combination of perceptual features that define the semantics of that category and that discriminate that category from other categories;
means for determining features of an image;
means for comparing features of the image to the sets of perceptual features of the semantic categories; and
means for classifying the image as belonging to one of the semantic categories if all of the required features and at least one of the frequently occurring features for that semantic category are present in the features of the image.

53. An apparatus as in claim 52, where the perceptual features and their combinations are derived through subjective experiments performed with human observers.

54. An apparatus as in claim 52, where the means for comparing further comprises means for computing a similarity measure between the features used to describe the semantic category and corresponding features determined from the image; and where the means for classifying further comprises means for assigning the image to that semantic category that corresponds to a highest value of the similarity measure.

55. A data processing system comprising a data processor and at least one memory comprising a stored program, the data processor operating in accordance with the stored program to form, for each semantic category of a plurality of semantic categories, a set of perceptual features comprising required features and frequently occurring features, where each semantic category is modeled through a combination of perceptual features that define the semantics of that category and that discriminate that category from other categories, said data processor operating in accordance with the stored program to determine features of an image, to compare features of the image to the sets of perceptual features of the semantic categories, and to classify the image as belonging to one of the semantic categories if all of the required features and at least one of the frequently occurring features for that semantic category are present in the features of the image.

56. An apparatus as in claim 55, where the perceptual features and their combinations are derived through subjective experiments performed with human observers.

57. An apparatus as in claim 55, where the data processor further operates when comparing to computer a similarity measure between the features used to describe the semantic category and corresponding features determined from the image; and where the data processor further operates when classifying to assign the image to that semantic category that corresponds to a highest value of the similarity measure.

58. A computer program as in claim 43, where said perceptual features and their combinations are derived through subjective experiments performed with human observers.

59. A computer implemented method for characterizing images and determining image similarity based on semantic meaning of images, comprising:
    performing subjective experiments with human observers to determine perceptual features of a plurality of images and to determine sets of semantic categories for the plurality of images, wherein each semantic category is modeled through a combination of perceptual features that define the semantics of that category and that discriminate that category from other categories;
    for each semantic category of a plurality of semantic categories, forming a set of perceptual features comprising required features and frequently occurring features;
    determining features of a query image;
    classifying the query image as belonging to one of the semantic categories if all of the required features and at least one of the frequently occurring features for that semantic category are present in the features of the image, wherein classifying further comprises computing a similarity measure between the perceptual features used to describe a semantic category and corresponding features determined from the query image; and
    assigning the query image to that semantic category that corresponds to a highest value of the similarity measure.

60. A computer implemented method for characterizing images and determining image similarity based on semantic meaning of images, comprising:
    performing subjective experiments with human observers to determine perceptual features of a plurality of images and to determine sets of semantic categories for the plurality of images, wherein each semantic category is modeled through a combination of perceptual features that define the semantics of that category and that discriminate that category from other categories;
    for each semantic category of a plurality of semantic categories, forming a set of perceptual features comprising required features and frequently occurring features;
    determining features of a query image;
    classifying the query image as belonging to one of the semantic categories if all of the required features and at least one of the frequently occurring features for that semantic category are present in the features of the image, wherein classifying further comprises computing a similarity measure between the perceptual features used to describe a semantic category and corresponding features determined from the query image, where the similarity measure comprises:

$$\operatorname{sim}(x, c_i) = \frac{1}{N_i} \prod_{j=1}^{M_i} \tau\left(RF_j(x|c_i), RF_j(c_i)\right) \cdot \sum_{j=1}^{N_i} \tau(FO_j(x|c_i), FO_j(c_i)),$$

where the query image is x, a semantic category is $c_i$, $\{RF_j(c_i)|j=1, \ldots, M_i\}$ is a set of $M_i$ required features, $\{FO_j(c_i)|j=1, \ldots, N_i\}$ is a set of $N_i$ frequently occurring features, $$\tau(a, B) = \begin{cases} 1, & (\exists i)\ a = b_i \\ 0, & (\forall i)\ a \neq b_i \end{cases}, \text{ and } B = \{b_i\}_{i=1, \ldots, l}; \text{ and}$$

assigning the query image to that semantic category that corresponds to a highest value of the similarity measure.

* * * * *